(12) United States Patent
Zhovnirovsky et al.

(10) Patent No.: US 11,766,185 B2
(45) Date of Patent: Sep. 26, 2023

(54) SYSTEMS AND METHODS FOR MINIMALLY INTRUSIVE DISPLAYS WITH HEART RATE MONITORING AND WORKOUTS

(71) Applicant: FLIPPER, INC., Albany, CA (US)

(72) Inventors: Yuri Zhovnirovsky, Albany, CA (US); Cory Borovicka, Oakland, CA (US); Paul M. Hanson, Carmel, CA (US); Anthony A. Ambuehl, Placerville, CA (US); Seyed Koosha Sadeghi Oskooyee, Phoenix, AZ (US)

(73) Assignee: Flipper Inc., Albany, CA (US)

( * ) Notice: Subject to any disclaimer, the term of this patent is extended or adjusted under 35 U.S.C. 154(b) by 0 days.

(21) Appl. No.: 17/405,641

(22) Filed: Aug. 18, 2021

(65) Prior Publication Data

US 2021/0369127 A1 Dec. 2, 2021

Related U.S. Application Data

(63) Continuation-in-part of application No. 17/135,974, filed on Dec. 28, 2020, which is a
(Continued)

(51) Int. Cl.
*A61B 5/024* (2006.01)
*A61B 5/00* (2006.01)
*A61B 5/11* (2006.01)

(52) U.S. Cl.
CPC ............ *A61B 5/02405* (2013.01); *A61B 5/11* (2013.01); *A61B 5/6802* (2013.01); *A61B 5/742* (2013.01)

(58) Field of Classification Search
CPC ............ G02B 27/0172; G02B 27/0093; G02B 2027/014; G02B 2027/0141; G02B 2027/0178; A61B 5/02427; A61B 5/6803; A61B 5/7445; A61B 5/20438; A61B 5/0408; A61B 5/486; A61B 5/0816; A61B 5/14542; A61B 5/4866; A61B 5/7264; A61B 5/1118; A61B 5/1116; A61B 5/7275; A61B 5/0077; A61B 5/02405; A61B 5/02055; A61B 5/02433; A61B 2503/10; A61B 2505/09; A61B 2560/0257; A61B 2562/0219; A61B 2562/0247; A61B 2562/029; G16H 50/30; G16H 50/20;
(Continued)

(56) References Cited

U.S. PATENT DOCUMENTS

| | | | |
|---|---|---|---|
| 4,526,473 A | 7/1985 | Zahn, III | |
| 4,796,987 A | 1/1989 | Linden | |
| 5,585,871 A * | 12/1996 | Linden | .................. G02C 11/00 351/158 |
| 10,012,506 B1 | 7/2018 | Monahan et al. | |
| 10,698,219 B1 | 6/2020 | Eisenhardt et al. | |

(Continued)

OTHER PUBLICATIONS

Copyright 2021, FORM Athletica, Inc., https://www.formswim.com, screen shot.

*Primary Examiner* — David Tung
(74) *Attorney, Agent, or Firm* — Fletcher Yoder, P.C.

(57) ABSTRACT

A system includes a minimally intrusive display system (MIDS) configured to be disposed on an eyewear. The MIDS includes a display system and a sensor system configured to provide for a sensor data. The MIDS further includes a processor configured to download a workout and to process the sensor data to monitor a user wearing the MIDS during the workout. The processor is further configured to display, via the display system, a workout progress based on the monitoring.

20 Claims, 22 Drawing Sheets

Related U.S. Application Data continuation-in-part of application No. 16/274,231, filed on Feb. 12, 2019, now Pat. No. 10,874,311.

(58) Field of Classification Search
CPC .............. A63B 24/0062; A63B 33/002; A63B 2024/0025; A63B 2024/0068; A63B 2071/0625; A63B 2071/065; A63B 2071/0655; A63B 2071/0666; A63B 2209/08; A63B 2209/10; A63B 2220/34; A63B 2220/18; A63B 2220/83; A63B 2220/51; A63B 2220/207; A63B 2220/833; A63B 2220/836; A63B 2220/75; A63B 2220/74; A63B 2220/04; A63B 2220/40; A63B 2220/73; A63B 2220/76; A63B 2220/72; A63B 2220/805; A63B 2220/80; A63B 2220/12; A63B 2220/16; A63B 2220/17; A63B 2220/30; A63B 2220/50; A63B 2220/62; A63B 2220/64; A63B 2220/803; A63B 2225/12; A63B 2225/50; A63B 2225/60; A63B 2225/74; A63B 2230/50; A63B 2230/75; G02C 11/10; G02C 7/086

See application file for complete search history.

(56) References Cited

U.S. PATENT DOCUMENTS

| | | | |
|---|---|---|---|
| 2003/0018274 A1 | 1/2003 | Takahashi et al. | |
| 2003/0138763 A1 | 7/2003 | Roncalez et al. | |
| 2003/0189484 A1 | 10/2003 | Rust et al. | |
| 2005/0078378 A1 | 4/2005 | Geist | |
| 2005/0225868 A1 | 10/2005 | Nelson et al. | |
| 2007/0109491 A1* | 5/2007 | Howell | A61B 5/02433 351/41 |
| 2009/0239710 A1 | 9/2009 | Shemesh et al. | |
| 2010/0030482 A1* | 2/2010 | Li | A61B 5/1123 702/19 |
| 2010/0304934 A1* | 12/2010 | Woodson | A63B 24/0062 482/8 |
| 2014/0059472 A1 | 2/2014 | Zhaiek et al. | |
| 2014/0161322 A1 | 6/2014 | Cheng et al. | |
| 2014/0213917 A1* | 7/2014 | Hobeika | A61B 5/02438 600/500 |
| 2016/0217324 A1* | 7/2016 | Burton | G06V 40/23 |
| 2019/0269968 A1 | 9/2019 | Eisenhardt et al. | |
| 2020/0285061 A1 | 9/2020 | Eisenhardt et al. | |
| 2022/0152458 A1 | 5/2022 | Eisenhardt et al. | |

* cited by examiner

SYSTEMS AND METHODS FOR MINIMALLY INTRUSIVE DISPLAYS WITH HEART RATE MONITORING AND WORKOUTS

CROSS-REFERENCE TO RELATED APPLICATION

This application is a continuation-in-part of U.S. Non-Provisional application Ser. No. 17/135,974, entitled "SYSTEMS AND METHODS FOR MINIMALLY INTRUSIVE DISPLAYS WITH HEART RATE MONITORING AND WORKOUTS," filed Dec. 28, 2020, which is a continuation-in-part of U.S. Non-Provisional application Ser. No. 16/274,231, entitled "SYSTEMS AND METHODS FOR MINIMALLY INTRUSIVE DISPLAYS WITH HEART RATE MONITORING," filed Feb. 12, 2019, (now U.S. Pat. No. 10,874,311, which issued on Dec. 29, 2020), each of which is hereby incorporated by reference in their entirety for all purposes.

BACKGROUND

The subject matter disclosed herein relates to displays, and more specifically, to minimally intrusive displays.

Certain activities, such as swimming, running, bicycling, and the like, may benefit from specific eyewear. For example, swim goggles may provide for enhanced underwater views and for eye protection from water. Similarly, sunglasses, motorcycle visors, ski goggles, and so on, may be worn to protect a wearer's eyes and to enhance the wearer's vision during certain activities. Some eyewear may incorporate displays. It may be beneficial to provide for minimally intrusive displays.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a system includes a minimally intrusive display system (MIDS) configured to be disposed on an eyewear. The MIDS includes a display system and a sensor system configured to provide for a sensor data. The MIDS further includes a processor configured to process the sensor data to derive a physiologic measurement. The processor is further configured to display, via the display system, the physiologic measurement, wherein the display system is disposed in the eyewear so that the physiologic measurement is only viewed when a user of the eyewear turns the user's pupil towards the display system at angle $\alpha$ from a forward direction.

In another embodiment, a non-transitory computer readable medium includes executable instructions which, when executed by a processor, cause the processor to receive a sensor data from a sensor system disposed in a minimally intrusive display system (MIDS) configured to be disposed on an eyewear. The executable instructions additionally cause the processor to process the sensor data to derive a physiologic measurement. The executable instructions additionally cause the processor to display, via a display system disposed in the MIDS, the physiologic measurement, wherein the display system is disposed in the eyewear so that the physiologic measurement is only viewed when a user of the eyewear turns the user's pupil towards the display system at angle $\alpha$ from a forward direction.

In yet another embodiment, a method includes receiving a first sensor data from a sensor system disposed in a minimally intrusive display system (MIDS) configured to be disposed on an eyewear. The method further includes processing the sensor data to derive a physiologic measurement. The method additionally includes displaying, via a display system disposed in the MIDS, the physiologic measurement, wherein the display system is disposed in the eyewear so that the physiologic measurement is only viewed when a user of the eyewear turns the user's pupil towards the display system at angle $\alpha$ from a forward direction.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
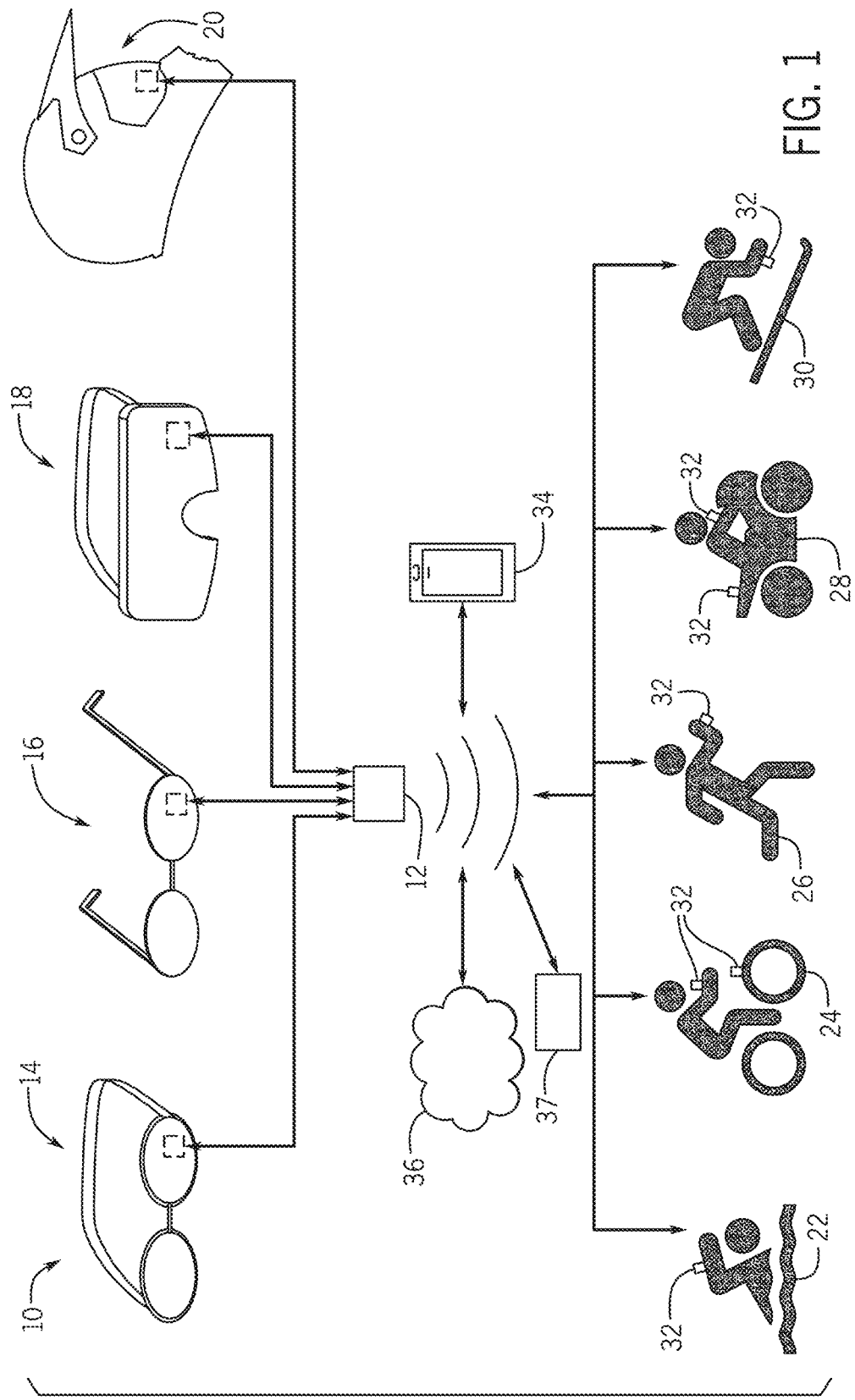
FIG. 1 is a block diagram of an embodiment of a sport-oriented system which includes one or more minimally intrusive display systems (MIDS)

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure may apply to a variety of eyewear, including sports-oriented eyewear such as swim goggles, sunglasses, ski goggles, motorcycle goggles, helmet visors, and so on. In certain embodiments, a minimally intrusive display system (MIDS) may be included in the eyewear, suitable for providing visual indications and feedback of ongoing user and/or sensor activities, as further described below. The MIDS may include a small form factor, such as 50×50 mm square, or less, that enables the user to more quickly identify useful information on a display while maintaining situational awareness. That is, the user may glance at information provided via a display included in the MIDS while still maintaining a field of view suitable for easy visualization of the surrounding environment. The MIDS may also include certain techniques to provide for heart monitoring of the user.

In certain embodiments, the MIDS may be removable and replaceable. For example, the user may toolessly remove the MIDS from a swim google and then place the MIDS into a set of sunglasses for use in a non-swimming activity. Indeed, the MIDS may be toolessly interchangeable between various types of eyewear. Additionally, the MIDS may include one or more processors that may interface with one or more sensors (internal sensors, external sensors) to derive certain performance metrics and/or feedback related to the user's activity.

For example, when swimming, feedback may be provided related to starts, turns, kicks, lap counts, breathing, speed, swim direction, and so on. When running, feedback may include speed, kick cadence, arm cadence, gait type, gait length, and the like. When bicycling, the feedback may include speed, pedaling cadence, power output, bicycle inclination, and so forth. Feedback for other activities is described below. The MIDS may communicate with external computing devices (e.g., cell phones, tablets, notebooks, cloud-based systems, smart watches, and the like) as well as with other MIDS to provide, for example, for virtual racing, improved coaching, sports social networking, and so on. Likewise, biometric information, such as heart rate, cardiac heart rest recovery time, health recovery time, heart variability, and so on, may be provided. By providing for the minimally intrusive techniques described herein, users may experience enhanced sports activities while improving their individual performance.

The MIDS may also include storage (e.g., memory) for storing a list of workouts. The workouts may be created by a manufacturer of the MIDS, by a user of the MIDS, by a social network, by a coach, by an artificial intelligence (AI), or any combination thereof. The workouts may then be categorized by one or more phases and/or attributes, such as workout duration, distance, effort expended, and so on. The user may select a workout from a workout library, for example, by searching via the phases and/or attributes. The workout may then be customized to the user, for example, based on user ability, the type of facility (e.g., pool, track, velodrome, etc.), based on progress made, and so on. The MIDS may then be worn by the user during the workout, and used to monitor and advance the user's activity based on the user's performance. By providing for a process for searching, downloading, executing, and analyzing workouts, the MIDS may enable a more efficient training process for the user.

Turning now to FIG. 1, the figure is a block diagram of an embodiment of a sport-oriented system 10 which may include one or more minimally intrusive display systems (MIDS) 12. As mentioned earlier, the MIDS 12 may be disposed in a variety of eyewear, such as swim goggles 14, sunglasses 16, ski goggles 18, and/or helmet visors 20. In certain embodiments, a MIDS 12 may be permanently attached to each of the goggles 14, sunglasses 16, ski goggles 18, and/or helmet visors 20. In other embodiments, the MIDS 12 may be removable and replaceable. For example, the MIDS 12 may be toolessly removed from the swim goggles 14 and then toolessly attached to the sunglasses 16, the goggles 18, the visor 20, and/or to another swim google 14. It is also to be understood that the list of eyewear shown is not limiting, and that other eyewear may be used with the MIDS 12, including prescription sports glasses, shooting glasses, automobile driving glasses, and so on.

In use, the MIDS 12 may provide for a minimally intrusive information display suitable for presenting a variety of information related to the activity being performed by wearer, such as swimming 22, bicycling 24, running 26, motorcycling 28, skiing 30, biometrics and so on. Accordingly, the MIDS 12 may include one or more internal sensors described in more detail below, suitable providing data correlative with the activity being performed. The MIDS 12 may additionally interface with a variety of external sensors 32 that may be worn by the user and/or disposed in certain equipment, suitable for providing data also correlative with the activity being performed.

The external sensors 32 may include accelerometers, gyroscopic sensors, speed sensors, location sensors (e.g., GPS, GLONASS systems), ambient temperature sensors, humidity sensors, altitude sensors, magnetometric sensors (e.g., compass systems), wind sensors (e.g., wind speed, wind direction), barometric pressure sensors, biometric sensors (e.g., pulse oximeters, body temperature sensors, electrocardiogram sensors, health informatics sensors [e.g., ISO/ IEEE 11073 sensors]), and the like, that may be communicatively coupled to one or more of the MIDS 12. For example, the MIDS 12 may include certain wireless systems, such as Wi-Fi (e.g., Institute of Electrical and Electronics Engineers [IEEE] 802.11X), cellular systems (e.g., high speed packet access [HSPA], HSPA+, long term evolution [LTE], WiMax), near field communications (NFC) systems, Bluetooth systems, personal area networks (PANs), Zigbee systems, Z-wave systems, wireless mesh systems, and the like, and so on, suitable for wirelessly communicating with the sensors 32. It is to be noted that the sensors 32 may be included in other systems, such as smart watches, smart bands, pedometers, wearable heart monitors, disposed in vehicles, and so on, which include wireless communications.

The MIDS 12 may additionally or alternatively interface with mobile devices 34 (e.g., cell phones, tablets, notebooks, laptops), a cloud-based system 36, and/or other external computing system 37. For example, the mobile devices 34, cloud-based system 36, and/or external computing systems 37 may be used to configure settings of the MIDS 12 as well as to communicate data during activities, such as during the sports activities 22, 24, 26, 28, and/or 30. In certain embodiments, the communications may be one-way communications. For example, a tablet 34 carried by a swimming coach (e.g., poolside coach) may receive information (e.g., lap count, inhalation/exhalation patterns, head movement, body roll, kick pattern, speed, etc.) incoming from the MIDS 12 and/or derive the information via data incoming from the MIDS 12. The information may then be used to give feedback to the wearer of the MIDS 12 during swimming activities 22.

In other embodiments, MIDS 12 communications may be two-way communications. In such embodiments, the wearer may receive information from external systems, such as the mobile devices 34, the cloud-based system 36, and/or other external computing systems 37 (e.g., computing systems including workstations, desktops, smart TVs, etc.) for configuration of the MIDS 12 and/or to provide feedback on the activity being performed by the wearer. For example, virtual coaching and training, gaming, social networking, customized workouts, and the like, may be provided via two-way communication, as described in more detail below.

It may be beneficial to illustrate example views of the MIDS 12 disposed on an eyewear system. Accordingly, and turning now to FIG. 2A, the figure is a front perspective view of an example MIDS 12 disposed on the swim goggles 14. In the depicted embodiment, the MIDS 12 is disposed on a left lens 40 of the swim goggles 14. However, in other embodiments the MIDS 12 may be disposed on a right lens 42 of the swim goggles 14. In yet other embodiments, the MIDS 12 may be disposable in either the left lens 40 or the right lens 40 based on the user's preference. For example, the MIDS 12 (or the entire left lens 40) may be toolessly removed and repositioned onto the right lens 42 (or right side) of the swim goggle 14. Indeed, in some embodiments the MIDS 12 may be removed by hand and then placed onto another type of eyewear (e.g., sunglasses 16, ski goggles 18, helmet visors 20), another set of swim goggles 14, and/or to the other side or lens of the swim goggles 14. The MIDS 12 may thus be self-contained, such as enclosed in a waterproof housing of size of 40 mm by 40 mm, 30 mm by 30 mm, 20 mm by 20 mm, 10 mm by 10 mm, or less.

Figure 2A:
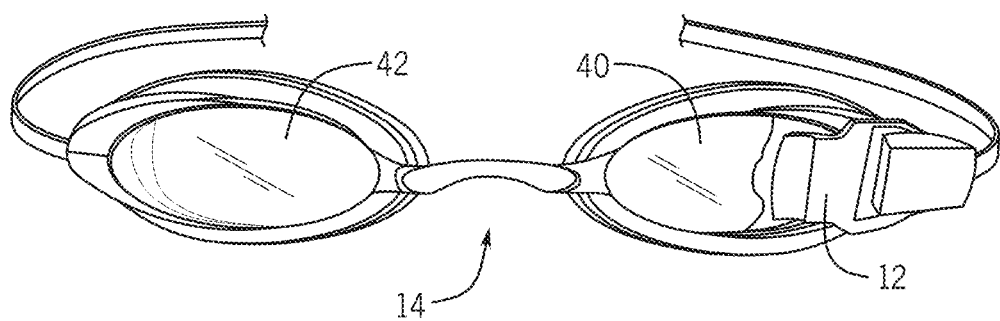
FIG. 2A is a front perspective view of an embodiment of the MIDS of FIG. 1 shown disposed on swim goggles.
Figure 2B:
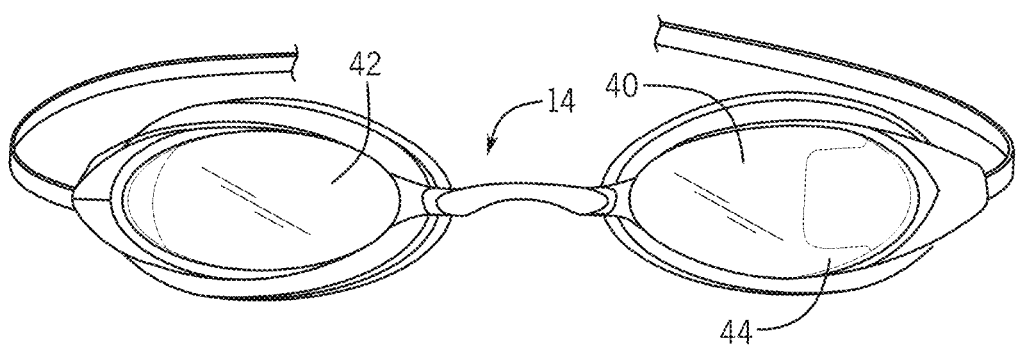
FIG. 2B is a front perspective view showing an embodiment of the swim goggles of FIG. 2A with the MIDS removed.

FIG. 2B is a front perspective view showing an embodiment of the swim goggles 14 with the MIDS 12 removed. More specifically, the figure illustrates an opening 44 suitable for deploying the MIDS 12 in situ. For example, the user may carry various swim goggles 14 with different opacities, goggles 14 for outdoor swimming, customizable goggles 14 (e.g., Swedish swim goggles), prescription goggles 14, and so on, and then easily insert the MIDS 12 into the opening 44 based on type of event, ambient conditions, and so forth. In certain embodiments, the MIDS 12 may mechanically couple with the lens 40 via an interference fit between edges of the opening 44 and an outer shell of the MIDS 12. Other coupling techniques may include tongue and groove fastening techniques, magnetic fasteners, mechanical latches, catches, and so on.

Figure 2C:
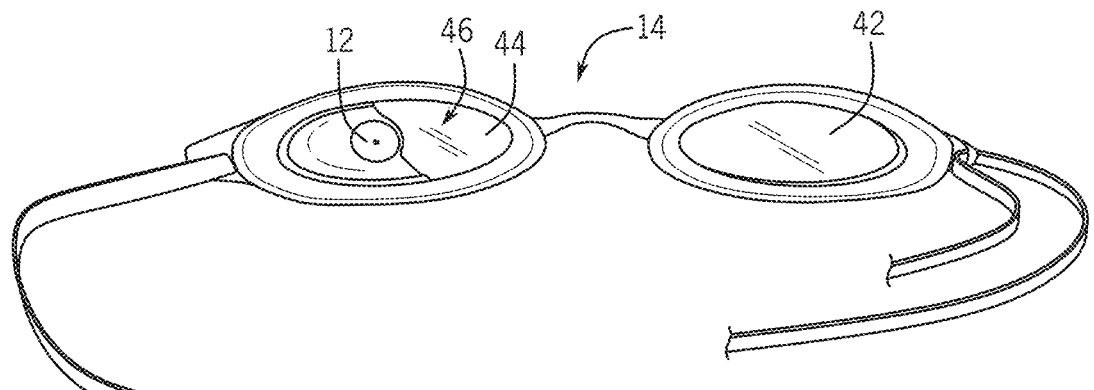
FIG. 2C is a rear perspective view illustrating an embodiment of the MIDS of FIG. 1 disposed in a lens of the swim goggles of FIGS. 2A and 2B.

In use, the MIDS 12 may provide for an improved field of view even with the MIDS 12 in place, as shown in FIG. 2C. More specifically, FIG. 2C is a rear perspective view illustrating an embodiment of the MIDS 12 disposed in the lens 44. As illustrated, the MIDS 12 may occlude only a small section of the lens 44, while leaving a larger section 46 unobstructed. Accordingly, the wearer may have and improved situational awareness and field of view when compared to larger display systems, useful in sports activities. It is to be note that while FIGS. 2A-2C depict the MIDS 12 using swim goggles 14 for context, the MIDS 12 may be disposed in openings 44 found in other eyewear, such as the sunglasses 16, the ski goggles 18, and/or the helmet visors 20.

Figure 3:
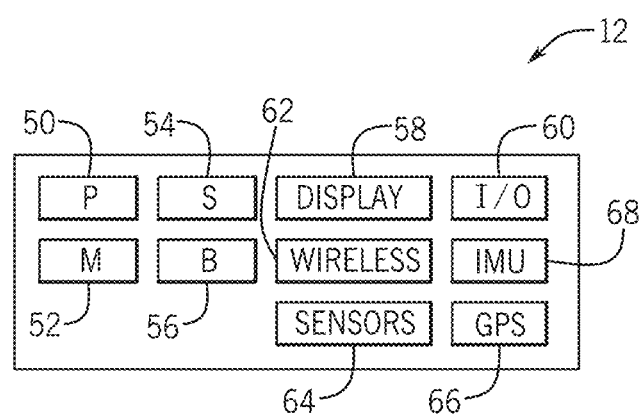
FIG. 3 is a system architecture block diagram of an embodiment of the MIDS of FIG. 1.

FIG. 3 is a system architecture block diagram of an embodiment of the MIDS 12. As depicted, the MIDS 12 may include one or more processors 50 and memory 52. The processor 50 may include "general-purpose" microprocessors, special-purpose microprocessors, application specific integrated circuits (ASICS), a reduced instruction set (RISC) processors, field programmable arrays (FPGAs), or some combination thereof. The memory 52 may include a volatile memory, such as random access memory (RAM), and/or a nonvolatile memory, such as ROM. The memory 52 may store a variety of information and may be used for various purposes. For example, the memory 52 may store processor-executable instructions (e.g., firmware or software) for the processor(s) 50 to execute. The MIDS 12 may also include a storage device 54. The storage device 54 may include a hard drive, a flash drive, a solid state storage medium, or combination thereof, suitable for storing digital data. Power for the MIDS 12 and its systems may be provided via a power supply system 56, which may include one or more rechargeable batteries chargeable via induction charging techniques and/or wired charging techniques.

In use, visual data (e.g., text, icons, images) may be provided via a display system 58. The display system 58 may include a low power micro display system (e.g., micro LED display) having, for example, a total size of 40 mm by 40 mm, 30 mm by 30 mm, 20 mm by 20 mm, 10 mm by 10 mm, or less. The display system 58 may be positioned in peripherally to the eye as shown in FIGS. 2A-2C, such that the display system 58 does not disturb forward vision. Peripheral positioning may include the corner of the eye (left or right), but it may also include the bottom or top of the eye. When placed at the top or bottom positions, two MIDS 12 may be used so that two display systems 58 are placed in both eyes, creating binocular vision.

When positioned as described, if the athlete or wearer is not looking at the display system 58 then the athlete doesn't see the information and is not disturbed by the MIDS 12. In other words, the display system 58 may appear invisible unless looked at directly. Additionally, by having a direct display system 58, as opposed to an indirect display system having prisms, mirrors, projectors, and so forth, the MIDS 10 may be manufactured in a smaller and more reliable form factor, suitable for providing useful information while also providing for situational awareness and a more open field of view.

In addition to or alternative to LED displays, the display system 58 may include one or more LED lights. Light feedback may be advantageous because it may not break exercise concentration or require deeper processing. Simple color lights may be used to indicate performance. For example, green would indicate good performance in swim turns, swim stroke, swim kick cadence, bike speed, run speed, bike cadence, run cadence, ski turns, motorcycle lean, and so on. Red may indicate when performance is not as desired. Accordingly, the MIDS 10 may be capable of filling the eyewear with colored light to provide feedback to the wearer.

Further, an input/output (I/O) system 60 may provide for other output modalities haptic output, and/or audio output. Haptic output may include force feedback such as "tapping" motions. Audio output may be provided via bone conduction, via wireless techniques (e.g., Bluetooth Advanced Audio Distribution Profile [A2DP], aptX), and/or via a waterproof audio port. Audio feedback may indicate a "good" noise when performance is desired, such as a chime, and a "bad" noise when performance is not as desired, such as a buzzer. Audio feedback may additionally or alternatively include a metronome-like sound played to help improve stroke count when swimming, cadence when biking and/or running, to keep track of elapsed time, and so on. The sound or "tappings" may also be set to operate adaptively by increasing/decreasing swimming stroke rate, bicycling/running cadence, skiing turns, and the like, by a fraction; and therefore slowly improving stroke rate, cadence, turning, and the like, without forcing the wearer to coarsely jump between rates. Audio output may also include voice coaching, music playing, and so on.

Input may be received via the I/O system 60, for example, via one or more buttons, and/or via touch sensors. The touch sensors may be suitable for receiving gesture inputs, such as swiping, tapping, pressing, holding, and so on. Accordingly, the user may switch modes, turn displays on and off, and so on. A wireless system 62 may also be included in the MIDS 12. As mentioned earlier, the wireless system 62 may include systems such as Wi-Fi (e.g., IEEE 802.11X), cellular systems (e.g., HSPA, HSPA+, long term evolution LTE, WiMax), near field communications (NFC) systems, Bluetooth systems including low power Bluetooth systems, personal area networks (PANs), Zigbee systems, Z-wave systems, wireless mesh systems, and the like, and so on, suitable for wirelessly communicating with other systems, such as the mobile system 34, the cloud-based system 36, and/or other external computing systems 37. Internal sensors 64 may include accelerometers, gyroscopic sensors, temperature sensors, ambient temperature sensors, humidity sensors, altitude sensors, magnetometric sensors (e.g., compass systems), barometric pressure sensors, biometric sensors (e.g., pulse oximeters, body temperature sensors, electrocardiogram sensors, health informatics sensors [e.g., ISO/IEEE 11073 sensors]), and the like.

In certain embodiments, internal sensors 64 include heart monitoring sensors such as photoplethysmographic (PPG) sensors, plethysmographic sensors, piezoelectric sensors, pulse oximetry sensors (e.g., light sensors), and so on, suitable for measuring heart rate, v, oxygen saturation, and so on. The internal sensors 64 may be placed at certain locations around the eye and/or nose areas to more accurately measure certain biological properties of the wearer, as shown in more detail below with respect to FIGS. 13-18.

A global positioning system (GPS) and/or GLONASS system 66 may also be included in the MIDS 12. The GPS system 66 may be used to provide for the MIDS 12 position of relative to a fixed global coordinate system, a fixed local coordinate system (e.g., indoor GPS), or a combination thereof. The GPS 66 may additionally use real time kinematic (RTK) techniques to enhance positioning accuracy. An inertial measurement unit (IMU) 68 may also be included, which may include one or more sensors, such as specific force sensors, angular rate sensors, accelerometers, gyroscopes, and/or magnetic field change sensors that may provide for the inertial measurements as the MIDS 10 moves. The IMU 68 may be used to provide for one or more degrees of freedom (DOF) measurements correlative with certain performance during activities 22, 24, 26, 28, 30 when the MIDS 12 is disposed on the wearer, as described in more detail with respect to FIG. 4. By placing a small heads up display in the MIDS 12 and/or by using audio feedback techniques as described, the athlete doesn't interrupt exercise cadence to consume information, unlike when using wrist-based devices. With wrist-based devices, the athlete typically has to stop swimming to see information or otherwise disrupt the activity such as by changing running cadence to allow the wrist to be raised and viewed, disrupting cycling pedaling cadence to examine a wrist or handlebar display.

Figure 4:
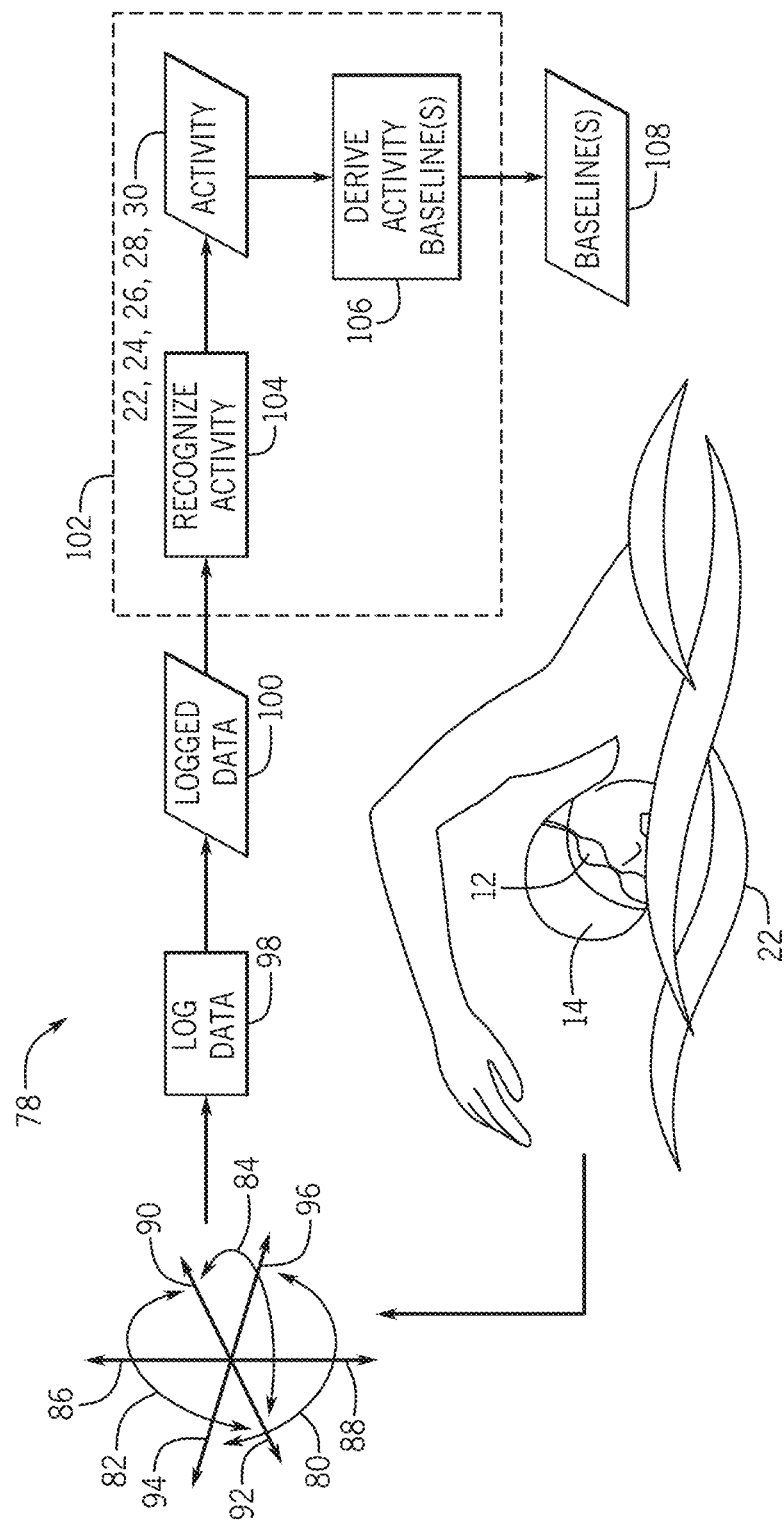
FIG. 4 is a flow diagram depicting an embodiment of a process suitable for deriving certain performance baselines for wearers of the MIDS of FIG. 1.

FIG. 4 depicts an embodiment of a process 78 suitable for deriving certain performance baselines for wearers of the MIDS 12. The process 78 or certain steps of the process 78 may be implemented as computer-executable instructions executed via the processor(s) 50, the mobile device 34, the cloud-based system 36, and/or other external computing systems 37. It to be understood that the process 78 may include steps that are optional, and that the steps may be performed in other order than the one shown.

In the depicted embodiment, the MIDS 12 is shown disposed in the swim goggles 14 during swimming activities 22. As mentioned above, the IMU system 68 may include sensors (e.g., as specific force sensors, angular rate sensors, accelerometers, gyroscopes, and/or magnetic field change sensors) that may be used to sense multiple degrees of freedom of the wearer's head. In the illustrated embodiment, 6 degrees of freedom are provided by the IMU system 68, including pitch 80, roll 82, yaw 84, up 86, down 88, left 90, right, 92, forward 94, and back 96. Accordingly, the MIDS 12 may receive and log (block 98) real-time data representative of the 6 degrees of freedom as the user undergoes an activity, such as swimming 22, resulting in logged data 100. The logged data 100 may also include data from the internal sensors 64 and/or the external sensors 32.

Certain techniques, such as a machine learning system 102, may be used to process the logged data 100 to recognize (block 104) the wearer's activity (e.g., activities 22, 24, 26, 28, 30) and the wearer's performance during the activity. For example, logged data 100 may be tagged as swim data, and the machine learning system 102 trained to recognize that the wearer was swimming. Likewise, the machine learning system may be trained to recognize any one of the activities 24, 26, 28, 30. The machine learning system 102 may then be used to derive (block 106) certain baselines 108 based on the activity. For example, for swimming 22, starts (e.g., block starts, outdoor swim starts), turns (e.g., flip turns, side turns, buoy turns), splits and sets, times, strokes (e.g., freestyle, breaststroke, butterfly, backstroke, sidestroke), kicking cadence, breathing patterns, head position during the swim, and so on, may be baselined. For example, a professional athlete may be "recorded" (e.g., used to provide the logged data 100) during swim turns and the machine learning system 102 may then train a neural network to recognize a "good" turn. This trained network then may become one of the baselines 108. The baseline(s) 108 may also be provided by statistical analysis. For example, the logged data 100 may be analyzed to derive medians, averages, ranges, which may then act as the baseline(s) 108. Accordingly, deviations, such as standard deviations, percentile deviations, quartile deviations, and so on, from the medians, averages, and/or ranges, may be outside of the baseline(s) 108. In this manner, baselines may be derived for "good" starts, strokes, kicking, breathing, head position, and so on.

Each activity 22, 24, 26, 28, 30 may be similarly processed to derive "good" (and "bad") baselines 108. For example, for bicycling 24, the baselines 108 may include recordings of flat terrain cadence, hill climbing cadence, sprinting, aero tuck head positioning, drafting, hill descent positioning, gear changes, and so on. For running 26 the baselines 108 may include flat terrain cadence, hill climbing cadence, hill descent cadence, arm rotation, foot landings, and so on. For motorcycle riding 28 the baselines 108 may include leaning on curved road sections, accelerating, braking (front wheel braking, rear wheel braking), and the like. For skiing 30 the baselines 108 may include parallel turning, edging, carving, cadence based on incline, and so on. The baselines 108 may also include biometrics, for example when biometric sensors 32 and/or 64 are used. The biometrics may include heart rate, body temperature, peripheral capillary oxygen saturation (e.g., SpO2 provided via pulse oximetry sensors), calories burned, heart rate, cardiac heart rest recovery time, health recovery time, heart variability, and the like.

The aforementioned baselines 108 are for example only and are non-limiting, as any number of baselines may be created based on a "recording" of a wearer performing some activity as well as manually through analysis of the logged data 100. It is to be noted that the baselines 108 are not restricted to logged data 100 recorded by professional athletes but may be derived for any user of the MIDS 12. For example, an amateur athlete may record" him or herself and then provide the recordings (e.g., logged data 100) to a coaching system for evaluation and/or to keep a record of progress, as further described below. The baselines 108 may also be used to analyze, in real-time, performance of the wearer of the MIDS 12 to provide feedback as to how to improve performance.

Figure 5:
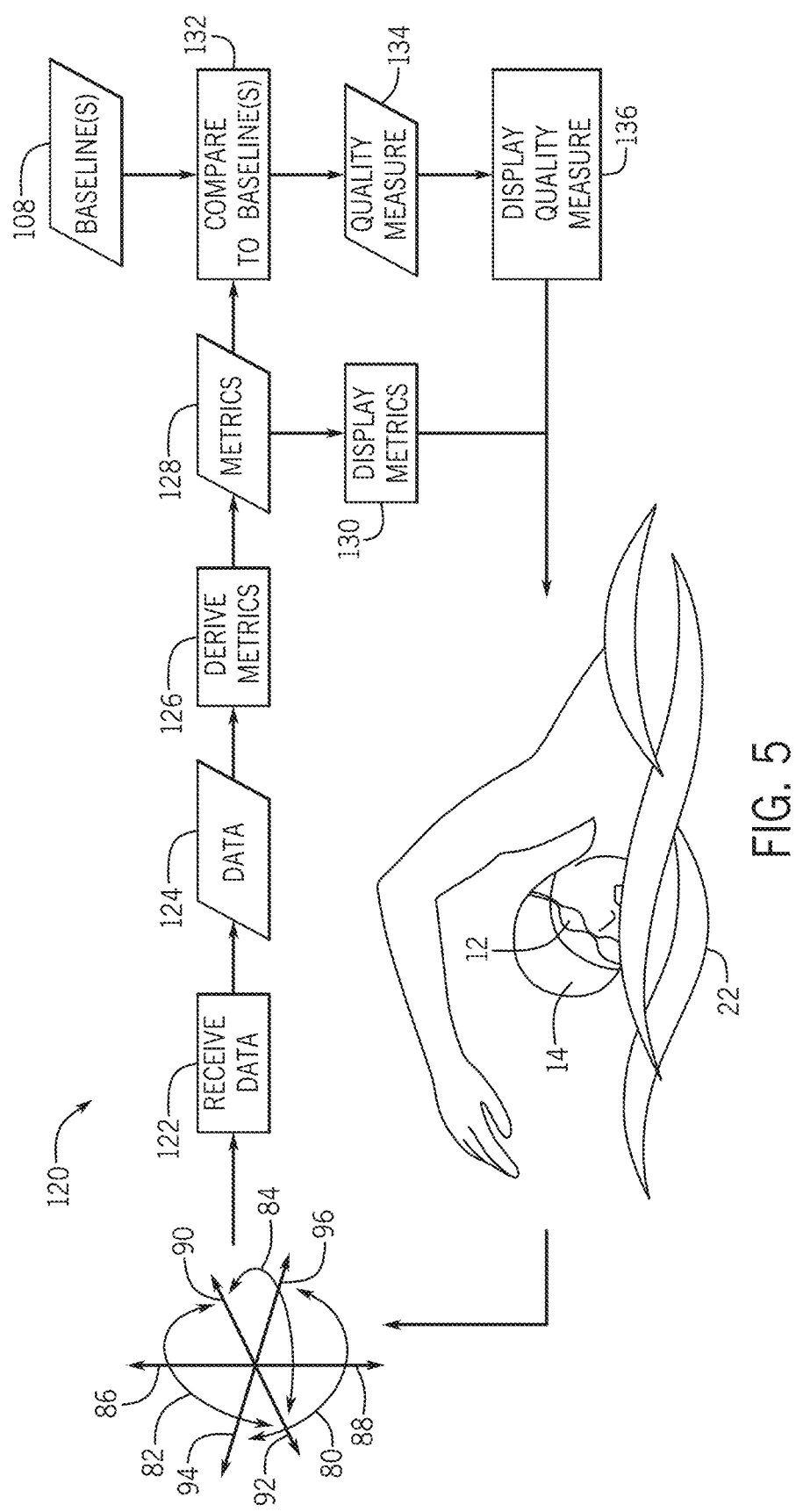
FIG. 5 is a flow diagram illustrating an embodiment of a process suitable for deriving certain performance metrics and/or feedback for wearers of the MIDS of FIG. 1.

FIG. 5 depicts an embodiment of a process 120 suitable for deriving certain performance metrics and/or feedback for wearers of the MIDS 12. The process 120 or certain steps of the process 120 may be implemented as computer-executable instructions executed via the processor(s) 50, the mobile device 34, the cloud-based system 36, and/or other external computing systems 37. It to be understood that the process 120 may include steps that are optional, and that the steps may be performed in other order than the one shown.

In the depicted embodiment, the wearer of the MIDS 12 may be performing the swimming activity 22 while training, competing, or simply for enjoyment of the activity 22. The MIDS 12 may enhance the activity 22 by providing for certain feedback. For example, as the wearer swims, the process 120 may receive (block 122) data 124, such as the degrees of freedom via the IMU system 68, as well as other sensed data from the sensors 32, 64. In certain embodiments, the data may be processed to derive (block 126) certain metrics 128. Deriving (block 126) the metrics 128 may include deriving the activity being performed, e.g., activity 22, 24, 26, 28, 30. Accordingly, the metrics 128 may be correlative with the activity being performed. For example, for swimming 22, the metrics may include speed, direction of travel, compass heading and/or location (for open water swimming), elapsed time, splits and sets, number of laps, type of stroke used, breathing metrics, head position metrics, kicking cadence, stroke cadence, body roll metrics, and so on.

For bicycling 24, the metrics 128 may include speed, direction of travel, compass heading and/or location, elapsed time, elapsed distance, as well as data gathered via external sensors 32 such as crankarm RPM (e.g., crankarm cadence), power output at the pedals (in Watts), current gear selected, bike odometer, and so on. For running 26 the metrics 128 may include speed, direction of travel, compass heading and/or location, elapsed time, elapsed distance, running cadence, arm cadence, foot placement, kicking cadence, and so on. For motorcycling 28 the activity metrics may include speed, direction of travel, compass heading and/or location, elapsed time, elapsed distance, leaning metrics, braking metrics, acceleration metrics, as well as data gathered via external sensors 32 such as MPG, engine RPM, odometer, gas tank level, coolant level, oil level, remaining range, error codes, and so on. For skiing 32 the metrics 128 may include speed, direction of travel, compass heading and/or location, elapsed time, elapsed distance, parallel turning metrics, edging metrics, carving metrics, cadence based on incline metrics, and so on.

The metrics 128 may also include biometrics, for example when biometric sensors 32 are used. The biometrics may include heart rate, body temperature, peripheral capillary oxygen saturation (e.g., SpO2 provided via pulse oximetry sensors), calories burned, heart rate, cardiac heart rest recovery time, health recovery time, heart variability, and the like. The metrics 128 may also include ambient metrics such as temperature, ambient pressure, altitude, humidity, and the like. Additionally, the metrics 128 may include GPS/GLONASS metrics such as current position and compass heading. Any one or more of metrics 128 may then be displayed (block 130), for example via the display system 58 and/or I/O system 60. As described earlier, the display system 58 may be positioned so that if the athlete or wearer is not looking at the display system 58 then the athlete doesn't see the information and is not disturbed by the MIDS 12. That is, the display system 58 may appear invisible unless looked at directly. In certain embodiments, the wearer may configure the MIDS 12 to create a user profile that may customize, for example, the set of metrics 128 to display for each of the activities 22, 24, 26, 28, 30.

The process 120 may also compare (block 132) the metrics 128 to the previously derived baseline(s) 108 to derive a quality measure 134. For example, a swim turn may include various metrics 128 such as head position at various points of the turn, speed of the head, leg positions/kicks, and/or body positions (via sensors 32 disposed on the body), through the turn. The metrics 128 may be compared (block 132) to metrics in the baseline(s) 108 to derive the quality measure 134. The comparison may include comparison by range (e.g., if the observed metric 128 is inside a range found in the baseline(s) 108), statistical comparisons (e.g., inside of a percentile, quartile, via standard deviation techniques, ANOVA techniques, MANOVA techniques, etc.), and/or AI comparisons (e.g., when the baseline(s) 108 include pattern recognition via neural networks, state vector machines, expert systems, fuzzy logic, and so on). The quality measure may be a binary measure, e.g., "good" and "bad", and/or a number such as a number between 1-10, 1-100, and the like, for example, denoting how close the metrics 128 are to the baseline(s) 108. Example quality measures for swimming include but are not limited to a swim turn quality measure, a kicking cadence quality measure, a body roll quality measure, a stroke performance quality measure, a head position quality measure, and so on. The quality measure 134 may then be displayed via the display system 58 and/or the I/O system 60. By providing for feedback during the performance of activities in a minimally intrusive manner, the MIDS 12 may enable improved training, competition, and an increased enjoyment of the activities.

Figure 6:
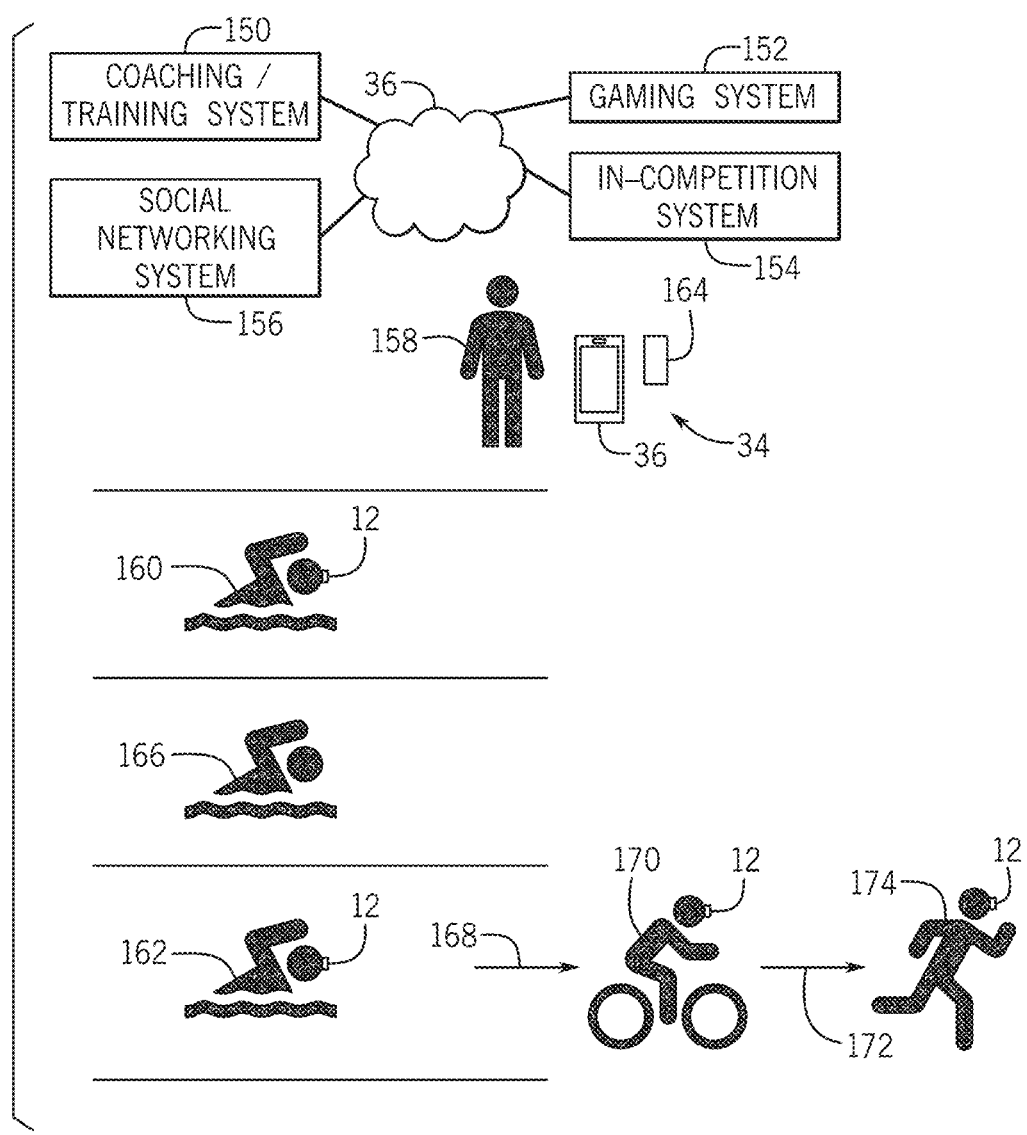
FIG. 6 is a block diagram illustrating an embodiment of a coaching/training system, a gaming system, an in-competition system, and a social networking system that may interface with the MIDS of FIG. 1.

FIG. 6 is a block diagram illustrates an embodiment of multiple systems, including a coaching/training system 150, a gaming system 152, an in-competition system 154, and a social networking system 156 that may interface with the MIDS 12 while worn by users. The systems 150, 152, 154, 156 may include software systems executable via the MIDS 12, the mobile device 34, the cloud-based system 36, and/or other external computing systems 37.

In the depicted embodiment, the coaching/training system 150 may receive, for example, the metrics 128 and/or data representative of the metrics 128 in real-time and/or offline and then provide for a repository of the MIDS 12 data as well as for feedback. For example, wearers may track daily, weekly, monthly progress by logging into the coaching/training system and visualizing or comparing, via a tablet, cell phone, computer display, and the like, training and/or competition metrics 128 as well as training and/or competition quality measures 134 throughout a desired time period (e.g., day week, month. The coaching/training system 150 may also provide feedback to improve performance. For example, the coaching/training system 150 may use AI, statistical, and/or human based analysis to analyze the metrics 128 and/or quality measures 134 and provide feedback on how to improve swim turns (e.g., suggestion on when to start a turn, speed of the turn, improvements to head position, improvements to body tuck, when to leg push, and so on). Similarly, for swimming 22, suggestions for stroke improvements, kicking cadence, breathing and breathing cadence, drafting, when to "attack" during competition, may be provided.

For running 24, the coaching/training system 150 may provide feedback such as suggestions on cadence, kicking, arm movement, pacing for distance, head lean, and so on. For bicycling 26, the coaching/training system 150 may provide feedback such as suggestions on speed, RPMs, when to get off the saddle, pedaling cadence, head position, gear shifting, drafting, and so on. For motorcycling 28, the coaching/training system 150 may provide feedback such as suggestions on leaning, gear changes, acceleration, braking, head position, and so on. For skiing 30, the coaching/training system 150 may provide feedback such as suggestions on where to look, parallel turning, edging, carving, stopping (e.g., v-stop, side stop), foot rotation, and so forth.

The coaching/training system 150 may also enable for remote or virtual coaching. For example, a human coach 158 may be located at a different geographic location from wearer 160 and from wearer 162. By using the coaching/training system 150, for example via a software application (e.g., app) 164, the coach 158 may receive real-time feedback, metrics 128, and/or quality measures 134 while the wearers 160, 162 are performing an activity, e.g., swimming 22. The coach 158 may then provide for recommendations on technique, changes to certain techniques, new training schedules, and so on. In some embodiments, the coach's 158 feedback may be displayed in the MIDS 12 (e.g., via display system 58, I/O system 60) or provided as audio. The coaching/training system 150 may also use the baselines 108 (e.g., heart rate, body temperature, peripheral capillary oxygen saturation (e.g., SpO2 provided via pulse oximetry sensors), calories burned, heart rate, cardiac heart rest recovery time, health recovery time, heart variability, and the like) to measure progress. For example, changes from the baselines 108 may then be used to determine workout changes, diet changes, recovery times, sleep times, and so on.

The gaming system 150 may provide for virtual racing against a virtual athlete 166 as well as against wearers 160 and 162 disposed in different geographic locations. The virtual athlete 166 may be an athlete that has been previously "recorded" with the techniques described herein. For example, the virtual athlete 166 may have been recorded in an Olympic size pool but then processed by the gaming system 150 to compete in open ocean swimming, in other pool lengths, and so on. Further, the virtual athlete 166 may be a previous recording from any wearer, including wearers 160, 162. The gaming system 150 may further process the wearer's recording to extrapolate a different type of swim, e.g., open ocean swim, during a virtual race. Further, the virtual athlete may be a fictional athlete created for virtual competition (e.g., aquaman). By connecting wearers 160, 162, at different locations, and by providing for one or more virtual competitors 166, the gaming system 150 may enable competitions across disparate geographic regions and with a broad category of competitors, including virtual athletes.

The in-competition system 154 may be used during actual competitions of the activities 22, 24, 26, 28, 30. Each competition may include a different set of rules as to what functionality the MIDS 12 may provide during the competition. For example, coaching functionality may be disabled. Accordingly, the MIDS 12 may receive a competition template disabling and/or enabling certain MIDS 12 functionality during the competition. The MIDS 12 may also be used in lieu of or in addition to competition smart tags, such as by tracking arrival at certain designated spots, providing for GPS tracking of competitors, providing for health information of competitors (including providing data from external health sensors), and so on.

FIG. 6 also illustrates "hand-off" capabilities of the MIDS 12 during multi-sport events, such as biathlons, triathlons, relay sports, and so on. In the illustrated embodiment, once the wearer 162 may have previously set up two MIDS 12 for triathlon. One MIDS 12 may be disposed in swim goggles 14 and the second MIDS 12 may be disposed in sunglasses 16. Once the wearer 162 exits the water and removes the swim goggles 14, the removal motion may then trigger a transition portion 168. During the transition portion 168 certain information may be tracked, such as a first triathlon transition time clock, to record transition times between swim-bike portions. Once the wearer 162 dons the sunglasses 16, the MIDS 12 on the sunglasses 16 may then take over and provide information during a bicycling portion 170 of the event. Once the bicycling portion 170 is complete, the wearer 162 may use the I/O system 60 to direct the second MIDS 12 disposed in the sunglasses 16 to begin a second transition 172. The second MIDS 12 may then, for example, begin a second triathlon transition time clock to record transition times between bike-run portions. The second MIDS 12 may then provide the wearer 162 information during a run portion 174 of the event. Data captured during the transitions may then be submitted to the systems 150, 152, 154, and/or 156. Indeed, the coaching/training system 150, the gaming system 152, the in-competition system 154, and/or the social networking system 156 may support data storage and analysis of multi-sport or relay sport data, including transitions 168, 172.

The social networking system 156 may enable meetings, virtual events, and data sharing between various users of the MIDS 12, including amateur users of various levels, professional users, and/or coaches. For example, the social networking system 156 may enable the discovery of other uses of similar performance levels. The users may form networks for training, competition, and/or advice. For example, a network may be formed via the social networking system 156 for users interested in learning how to swim using the butterfly stroke. The social networking system 156 may then coordinate training meets, including virtual meets, coaching, and progress tracking amongst the group, virtual competitions for group members, creation of virtual awards and points earned, and so on. Coaches may sign up via the social networking system 156 and advertise their expertise. The coaches may then provide services via the coaching/training system 150 and the MIDS 12. The social networking system 156 may thus be communicatively coupled to the systems 150, 152, 154, to share data, to share functionality, and/or to provide for a single login into all systems 150, 152, 154, 156.

Figure 7A:
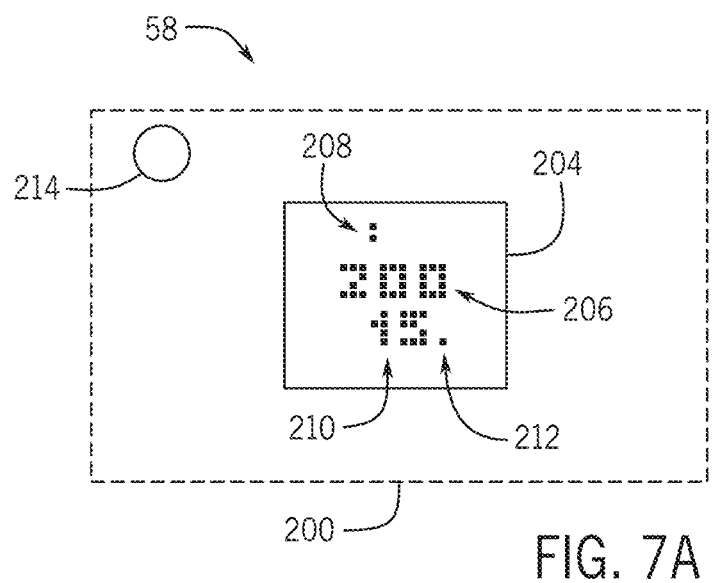
FIG. 7A is a diagram illustrating an embodiment of a display system of the MIDS of FIG. 1 showing text.
Figure 7B:
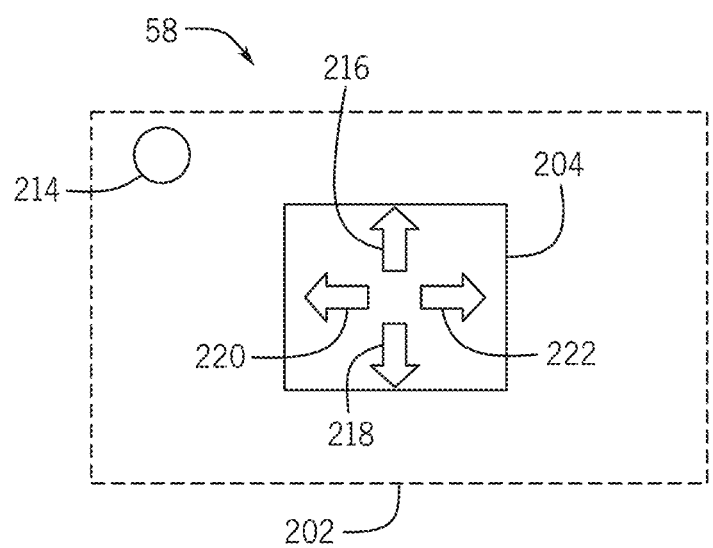
FIG. 7B is a diagram illustrating an embodiment of a display system of the MIDS of FIG. 1 showing images.

FIGS. 7A and 7B illustrate embodiments of certain areas 200, 202 of the MIDS 12 that may include the display system 58. In the embodiment depicted in FIG. 7A, the areas 200 includes a LED pixel display 204 that is shown displaying text. More specifically, the display 204 is displaying a time 206, a minute separator 208, a lap counter 210, and a swim indicator 212. The time displayed is thus 2:00 minutes, with 15 laps counted while still swimming. The display 204 may be small in size, such as between 10 mm by 10 mm to 40 mm by 40 mm or less. Accordingly, the display 204 may be disposed in a corner of eyewear to provide for a minimally intrusive display.

Further, FIG. 7A illustrates that the display system 58 may include a LED light 214, such as a multi-color LED. In use, the LED light 214 may be turned on at one or more colors based on the metrics 128 and/or the quality measure 134 derived during the various activities 22, 24, 26, 28, 30. For example, the color red may be displayed if certain metrics 128 and/or quality measures 134 are below a certain threshold, and the color green may be displayed if the metrics 128 and/or quality measures 134 are above the threshold. The light 214 and/or display 204 may be customizable by the wearer. For example, the wearer may select which of the various metrics 128 to be displayed as text, such as but not limited to speed, elapsed distance, elapsed time, splits, sets, laps counted, kicking cadence, and stroke cadence. The quality measures 134 may also be customized by the wearer to select which ones are be displayed as text, such as "good turn", "bad turn", "slow kick", "fast kick", and so on.

FIG. 7B illustrates the use of icons on the display 204. That is, in addition to text, icons may also be displayed. For example, the illustrated embodiments show an up arrow 216, a down arrow 218, a left arrow 220, and a right arrow 222. The arrows 216, 218, 220, 222 may be used to provide directions during certain activities as well as to provide feedback. For example, the up arrow 216 may indicate that a swimmer is swimming towards a desired direction during an outdoor swim, and when the swimmer strays form the desired direction, the left arrow 220 may be flashed to indicate to the swimmer to swim towards his or her left side to get back to the desired swim direction. Likewise, the right arrow 22 may be flashed to indicate to the swimmer to swim towards his or her right side to get back to the desired swim direction.

The up arrow 216 may also be displayed, akin to a "thumbs up", when a desired metric 128 and/or performance measure 134 is reached, the down arrow 218 may be displayed if the metric 128 and/or performance measure 134 is not reached. It is to be noted that other icons may be used, such as emoji (e.g., thumbs up icon, thumbs down icon, smiley face, sad face, and so on).

Figure 8:
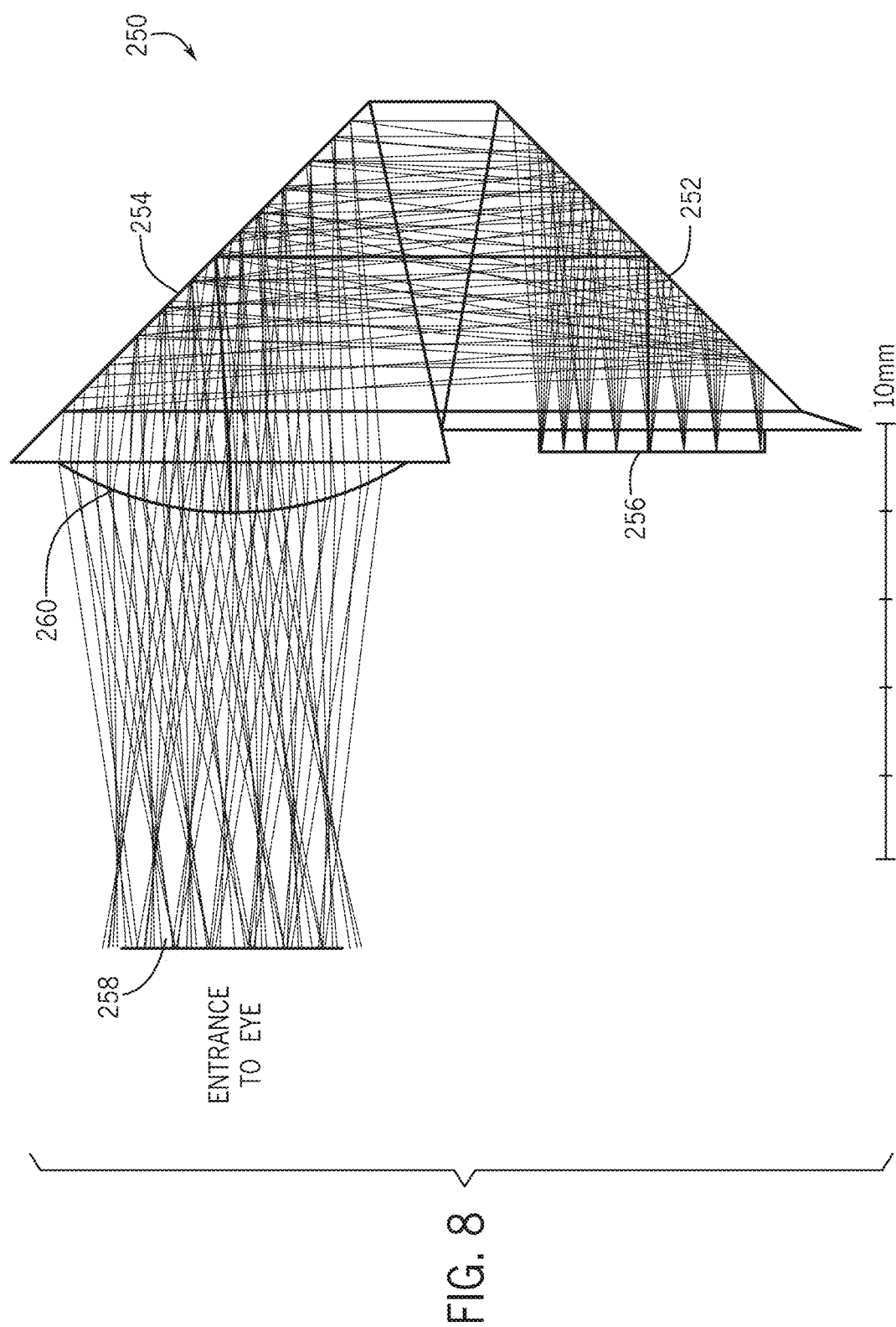
FIG. 8 is a schematic view of an embodiment of a double mirrored display system that may be included in the MIDS of FIG. 1.

FIG. 8 is a schematic view of an embodiment of a double mirrored display system 250 that may be included in the display system 58. The double mirrored display system 250 may use two mirrors 252 and 254 (e.g., "folded" mirrors) to increase a track length of the double mirrored display system 250, thus providing for a suitable presentation of visual information in a more compact package. That is, the mirrors 252 and 254 enable light to travel from a projective display system 256 into an eye entrance 258 with travel length or track length longer than directly projecting the light into the eye entrance 258. Accordingly, an improved view of data projected via the projective display system 256 may be provided.

The projective display system 256 (e.g., LCD, laser, etc.), which may be disposed on a printed circuit board (PCB). As light exits the projective display system 256, it then reflects off of the first mirror 252. The first mirror 252 may include a curvature, thus acting as a first lens suitable for magnifying the projected images. The light may then reflect off of the second mirror 254. The second mirror 254 may include a slight curvature to act as a slight correcting lens. The light may then be further enhanced via a normal aspheric lens surface 260. In some embodiments, the aspheric lens surface 260 may include a surface profile designed to reduce or to eliminate spherical and optical aberrations. In one embodiment, all components of the double mirrored display system 250 (e.g., the mirrors 252, 254, surface 260) may be manufactured as a single piece, for example, a piece molded in polymethyl methacrylate (PMMA), Polycarbonate, Zeonex, and so on. Additionally, the double mirrored display system 250, and indeed a variety of displays incorporated in the display system 58, may be disposed so that during the activity (e.g., activities, 22, 24, 26, 28, 30) the user may have a clear view of the activity and then with a slight movement of the eye, see information displayed via the display system 58 as further described below with respect to FIGS. 9-12.

Figure 9:
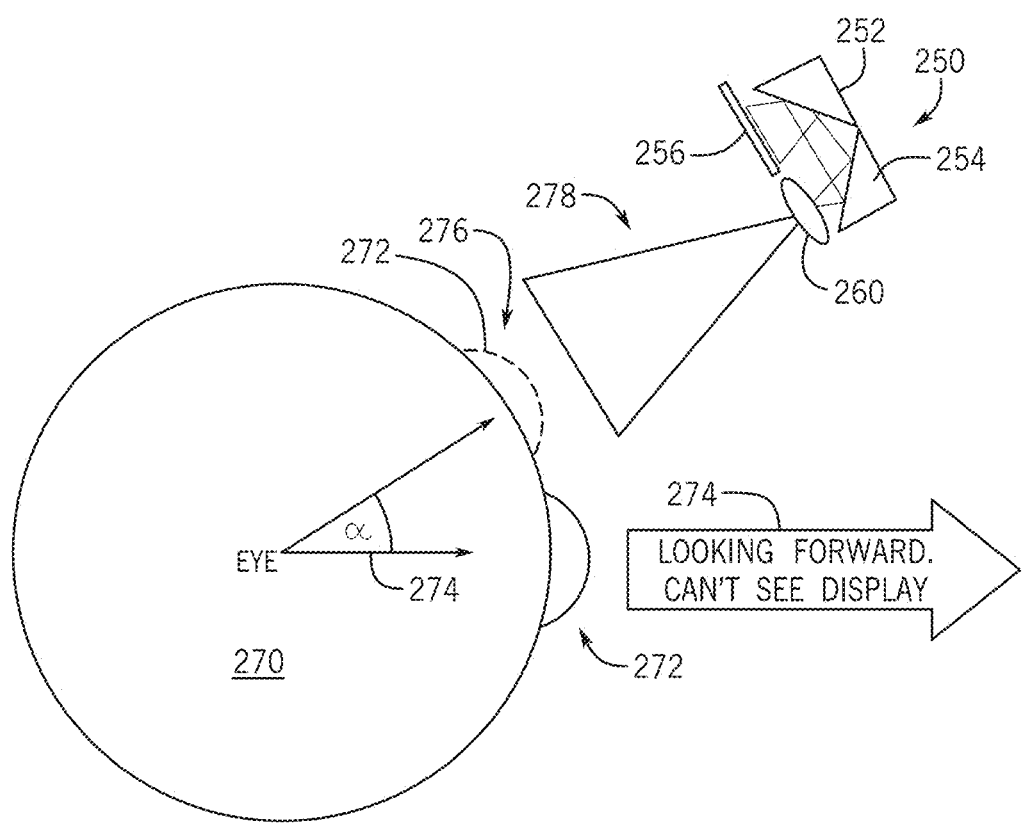
FIG. 9 is a schematic top view of an embodiment of the double mirrored display system of FIG. 8.

FIG. 9 is a schematic top view of an embodiment of the display system 58 where the display system 58 includes the double mirrored display system 250. In the depicted embodiment, the user's eye 270 is shown with the pupil 272 looking in a forward direction 274 away from the head (e.g., direction such that when both eyes are looking in the forward direction the corresponding vectors 274 for each eye are parallel to each other and to a plane that extends between and separates the frontal sinuses, bisecting the nose). When looking in the forward direction 274, the eye may not see information from the display system 250 and/or the display system 250 itself. Indeed, the user may look straight ahead during performance of the activities 22, 24, 26, 28, and/or 30 and have an unobstructed view. When the user then decides to receive information, such as information 130, 134 provided by the double mirrored display system 250, the user may glance to a side so that the pupil 272 moves from the forward direction 274 towards a position 276. That is, when the user moves the pupil 272 a certain angle $\alpha$ away from the forward direction 274 and towards the double mirrored display system 250, the user may now see information presented by the double mirrored display system 250. For example, at position 276, the pupil may enter the eye box 278 so that the light projected via the double mirrored display system 250 is now visible. In certain embodiments, the angle $\alpha$ may be between 10° to 90°. In certain embodiments, the display system 58 may include an OLED display to present visual information.

Figure 10:
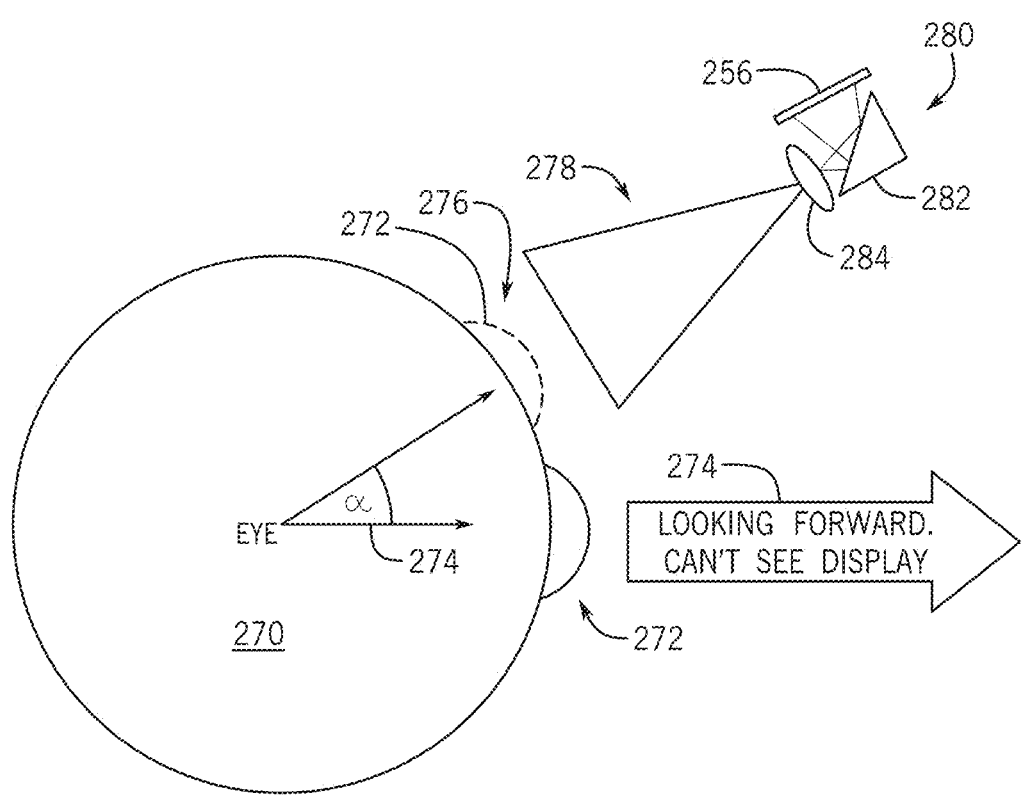
FIG. 10 is a schematic top view of an embodiment of a single mirrored display system that may be included in the MIDS of FIG. 1.

FIG. 10 illustrates a schematic top view of an embodiment of the display system 58 where the display system 58 includes a single mirrored display system 280. In the depicted embodiment, the user's eye 270 is shown with the pupil 272 looking in the forward direction 274 away from the head. As mentioned above, when looking in the forward direction 276, the pupil 272 may not see information provided via the single mirrored display system 280 or the single mirrored display system 280 itself.

As illustrated, the projective display system 256 may project information, such as information 130, 134, via light. The light may reflect off of a mirror 282, and then be further modified via optics 284, which may include a lens or lenses, including correcting lens or lenses, aspheric lens or lenses, or a combination thereof. The single mirrored display system 280 may include a light travel length or track length longer than directly projecting the light into the eye 270, but shorter than the light travel length of the double mirrored display system 250. The user may look straight ahead, e.g., in the forward direction 274, during performance of the activities 22, 24, 26, 28, and/or 30 and have an unobstructed view. When the user then decides to receive information, such as information 130, 134 provided by the single mirrored display system 280, the user may glance to a side so that the pupil 272 moves from the forward direction 274 towards a position 276. That is, when the user moves the pupil 272 a certain angle $\alpha$ away from the forward direction 274 and towards the single mirrored display system 280, the user may now see information presented by the single mirrored display system 280. For example, at position 276, the pupil may be able to see inside of the eye box 278 so that the light projected via the single mirrored display system 280 is now visible. In certain embodiments, the angle $\alpha$ may be between 10° to 90°.

Figure 11:
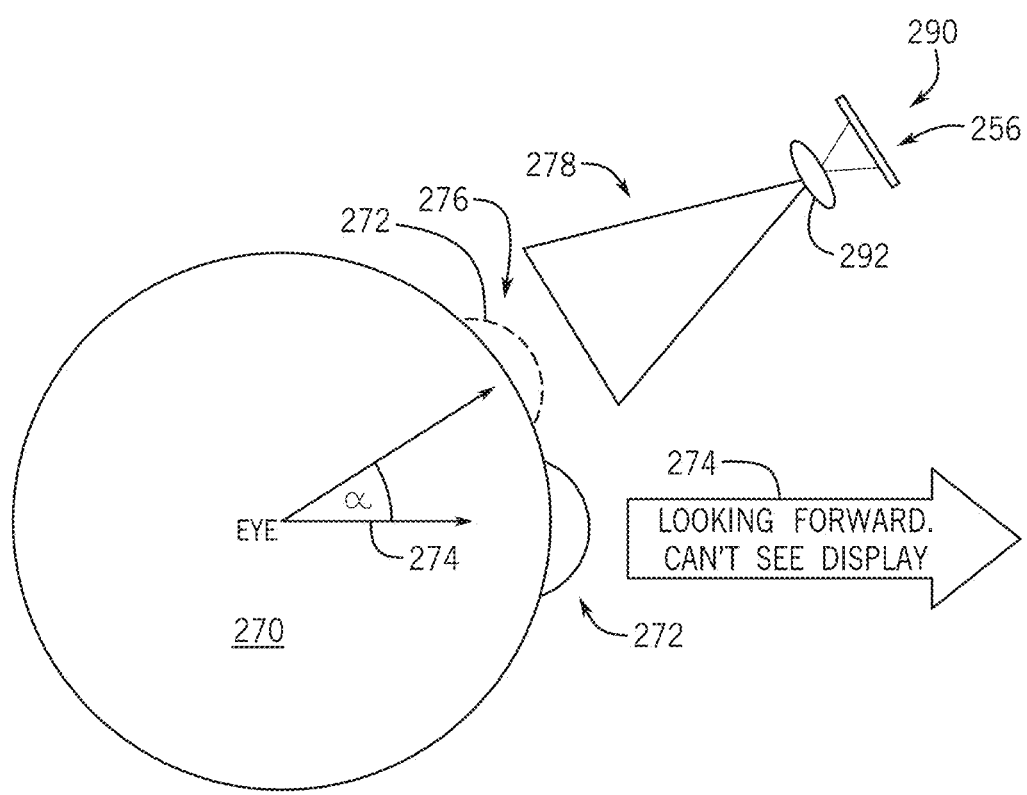
FIG. 11 is a schematic top view of an embodiment of a direct optical display system that may be included in the MIDS of FIG. 1.

FIG. 11 illustrates a schematic top view of an embodiment of the display system 58 where the display system 58 includes a direct optical display system 290. In the depicted embodiment, the user's eye 270 is shown with the pupil 272 looking in the forward direction 274 away from the head. As mentioned above, when looking in the forward direction 276, the pupil 272 may not see information provided via the direct optical display system 290 or the direct optical display system 290 itself.

As illustrated, the projective display system 256 may project information, such as information 130, 134, via light. The light may then be further modified via optics 292, which may include a lens or lenses, including correcting lens or lenses, aspheric lens or lenses, or a combination thereof. The direct optical display system 290 may include a light travel length shorter than the light travel length of the double mirrored display system 250. The user may look straight ahead, e.g., in the forward direction 274, during performance of the activities 22, 24, 26, 28, and/or 30 and have an unobstructed view. When the user then decides to receive information, such as information 130, 134 provided by the direct optical display system 290, the user may glance to a side so that the pupil 272 moves from the forward direction 274 towards a position 276. That is, when the user moves the pupil 272 a certain angle $\alpha$ away from the forward direction 274 and towards the direct optical display system 290, the user may now see information presented by the direct optical display system 290. For example, at position 276, the pupil may be able to see inside of the eye box 278 so that the light projected via the direct optical display system 290 is now visible. In certain embodiments, the angle $\alpha$ may be between 10° to 90°.

Figure 12:
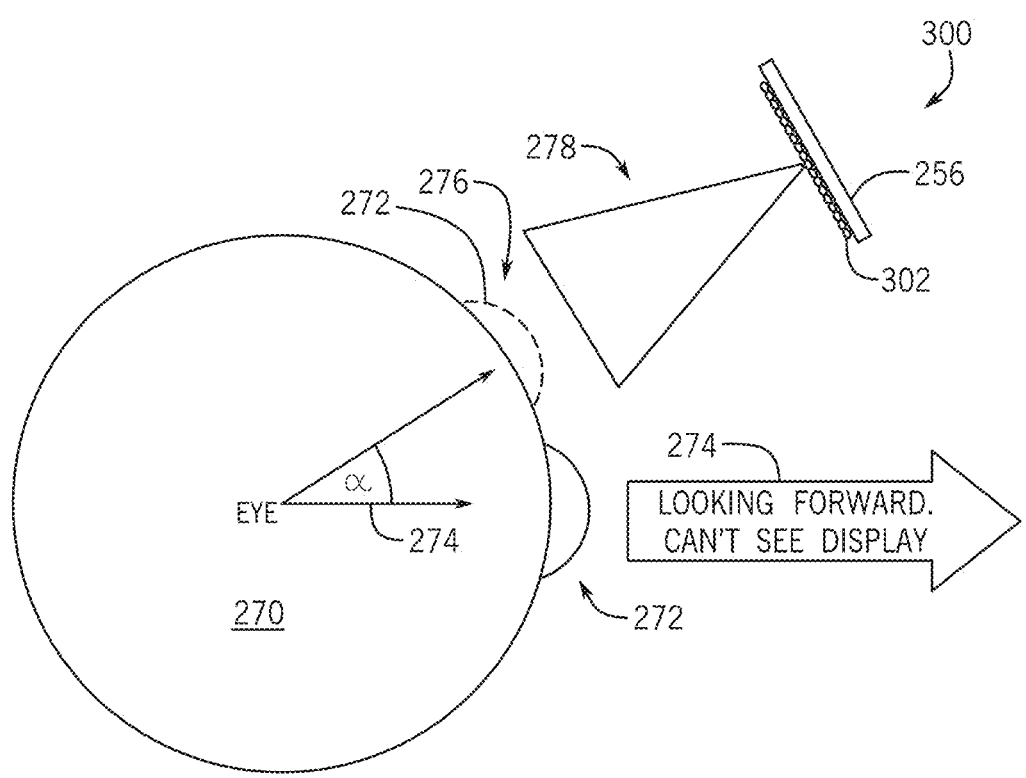
FIG. 12 is a schematic top view of an embodiment of a direct display system that may be included in the MIDS of FIG. 1.

FIG. 12 illustrates a schematic top view of an embodiment of the display system 58 where the display system 58 includes a direct display system 300. In the depicted embodiment, the user's eye 270 is shown with the pupil 272 looking in the forward direction 274 away from the head. As mentioned above, when looking in the forward direction 276, the pupil 272 may not see information provided via the direct display system 300 or the direct display system 300 itself.

As illustrated, the projective display system 256 may project information, such as information 130, 134, via light. The light may then be further modified via microlens or light-field projection optics 302. The microlens(es) may include diameters less than a millimeter, and may include gradient-index (GRIN) lenses, micro-Fresnel lenses, binary-optic lenses, and so on. The light-field projection optics may include lenslet arrays, projective arrays, and so on. The direct display system 300 may include a light travel length shorter than the light travel length of the double mirrored display system 250. The user may look straight ahead, e.g., in the forward direction 274, during performance of the activities 22, 24, 26, 28, and/or 30 and have an unobstructed view. When the user then decides to receive information, such as information 130, 134 provided by the direct display system 300, the user may glance to a side so that the pupil 272 moves from the forward direction 274 towards a position 276. That is, when the user moves the pupil 272 a certain angle $\alpha$ away from the forward direction 274 and towards the direct display system 300, the user may now see information presented by the direct display system 300. For example, at position 276, the pupil may be able to see inside of the eye box 278 so that the light projected via the direct display system 300 is now visible. In certain embodiments, the angle $\alpha$ may be between 10° to 90°.

It is to be understood that while the various display systems, e.g., systems 58, 250, 280, 290, 300 are shown as disposed on a side of a lens (e.g., side of lens of swim goggles 14, sunglasses 16, ski goggles 18, visor 20) in the figures above, the various display systems, e.g., systems 58, 250, 280, 290, 300 may be disposed on top/bottom of lenses or in other portions of the swim goggles 14, sunglasses 16, ski goggles 18, and/or visor 20 that are visible when placed over the eyes. Accordingly, the angle $\alpha$ away from the forward direction 274 may point towards any portion of the swim goggles 14, sunglasses 16, ski goggles 18, and/or visor 20, including lens portions, that are visible by moving the pupil 272 away from the forward direction 274.

Figure 13:
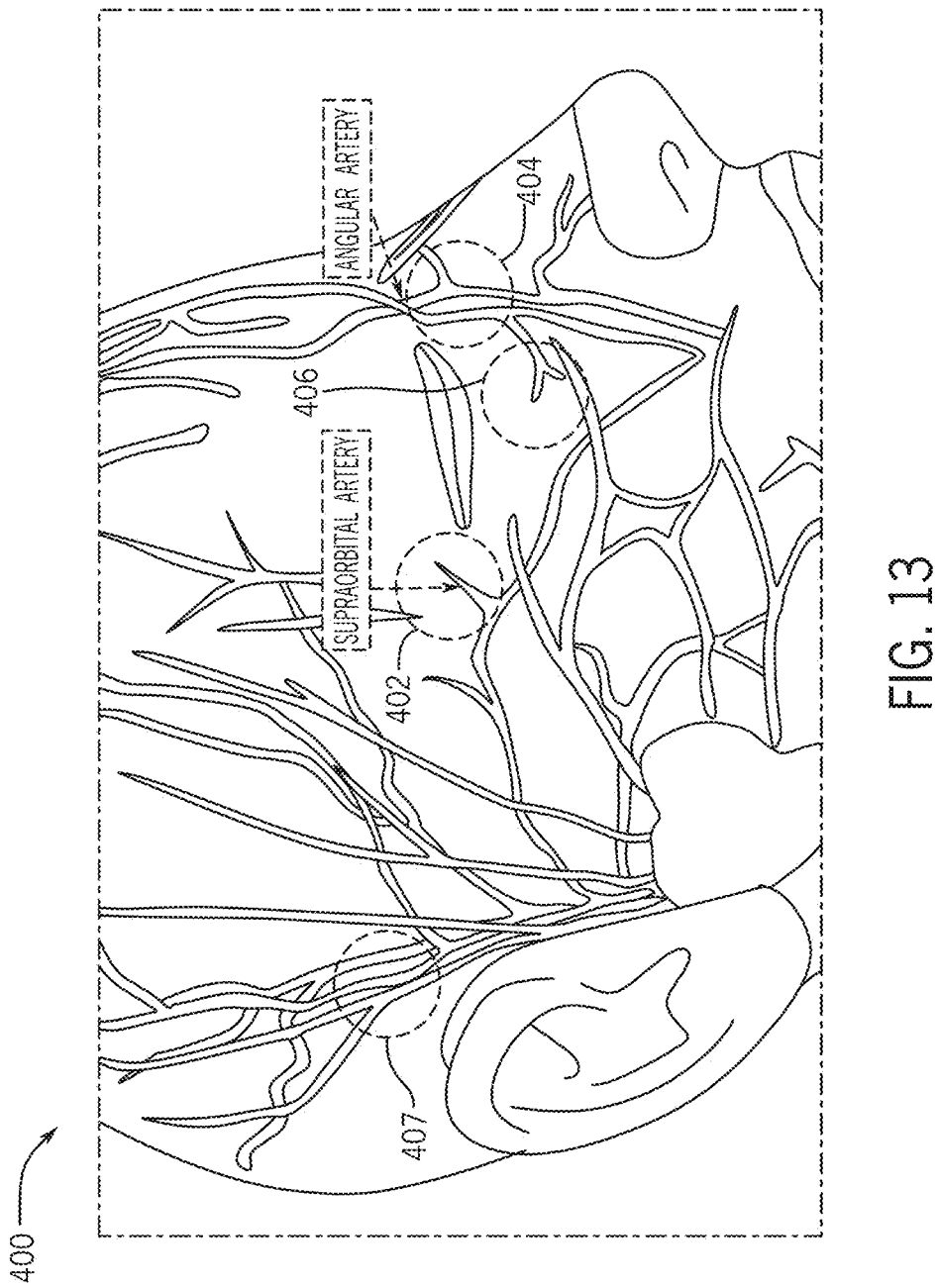
FIG. 13 is a perspective view of a human muscle and capillary head region showing placements for certain of embodiments of sensors included in the MIDS of FIG. 1.

Turning now to FIG. 13, the figure is a perspective view of a human muscle and capillary head region 400 showing placements for certain of the sensors 32, 64. For example, when using photoplethysmographic (PPG) and/or piezoelectric sensors, a supraorbital artery region 402, a first angular artery region 404, a second angular artery region 406, and/or a temporal artery region 407 may improve measurement quality. Likewise, a temporal artery location 407 may be used. The PPG sensors 32 and/or 64 may use a light emitting diode (LED) to shine light at the user's skin and then measure the returning light. Differences between outgoing and returning light may be used to determine heart rate, to obtain a volumetric measurement (e.g., plethysmogram) for the regions 402, 404, 406, 407 and the like. The heart rate and/or volumetric measurement may be used to monitor, cardiac cycle, respiration, hypovolemia, and/or hypervolemia.

For example, the processor(s) 50 may include algorithms that take as input signals from the PPG sensors 32 and/or 64 and then derive heart rate, cardiac cycle stages (e.g., 1 Isovolumic relaxation, 2a Inflow: (Ventricular filling), 2b Inflow: (Ventricular filling with Atrial systole), 3 Isovolumic contraction, 4 Ejection: Ventricular ejection), respiration (e.g., due to variance in the intrapleural pressure), fluid volumes and so on. For example, the data may be used to derive a Wiggers diagram, a pseudo electrocardiogram, a pseudo phonocardiogram, and so on. SpO2 may also be derived via the PPG sensors 32 and/or 64, and may be further used to estimate VO2Max, where VO2 is the volume of oxygen uptake. For example, changes in oxygen may be used to determine a rate at which oxygen is being used during physical activity. In certain embodiments, cardiac output (Q) may be derived by calculating stroke volume times heart rate. Both the stroke volume and the heart rate may be derived by the PPG sensors 32 and/or 64. An arterio-venous difference or A-VO2 difference may also be derived, for example with one PPG sensor 32 and/or 64 disposed in an arterial site and a second PPG sensor 32 and/or 64 in a venous site. Fick's equation: VO2=Q×A-VO2 difference, may then be used to calculate VO2 max.

The piezoelectric sensors 32 and/or 64 may use a piezoelectric effect (e.g., electric signals generated by an applied mechanical force such as a tap) to detect pulse rate. For example, as the supraorbital and/or angular artery expands and contracts through the cardiac cycle, the piezoelectric sensors 32 and/or 64 may provide a signal that correlative with volumetric changes in the supraorbital and/or angular arteries. The piezoelectric signals may then be used to derive the heart rate, cardiac cycle stages, fluid volumes, and the like. It is to be understood that multiple sensors types of the sensors 32 and/or 64 may be used, including PPG sensors, piezoelectric sensors, resistance-based sensors, cameras, body temperature sensors, electrocardiogram sensors, health informatics sensors (e.g., ISO/IEEE 11073 sensors), and so on.

Because of the placement, for example in regions 402, 404, 406, and/or 407, the techniques described herein may improve accuracy and result in a more compact MIDS 12 suitable for providing the MIDS 12 in a hydrodynamic shape to improve drag coefficients and minimize turbulence. In certain embodiments, the MIDS 12 may only include internal sensors 64. Accordingly, the user, such as a competitive swimmer, may receive more accurate biofeedback data without having to wear chest straps, limb straps (watch straps, leg straps), and so on.

Figure 14:
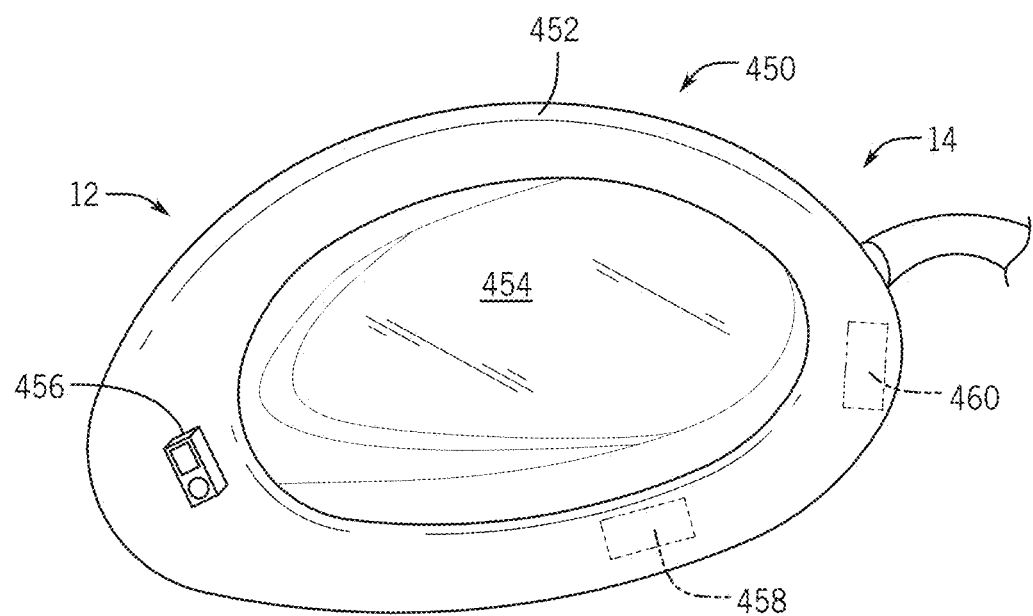
FIG. 14 is a rear perspective view of an embodiment of the MIDS of FIG. 1 when provided in a swim goggles form factor.

FIG. 14 is a rear perspective view of an embodiment of the MIDS 12 when provided in a swim goggles 14 form factor. In the depicted embodiment, the swim googles 14 include a seal or gasket system 450. The gasket system 450 may include a unibody silicone gasket 452 surrounding a translucent or transparent eyepiece 454. In use, the gasket 452 may comfortably seat the eyepiece 454 against a swimmer's eye socket, providing for a watertight seal during water immersion. Also shown are a PPG sensor 456 and two piezoelectric sensors 458 and 460. The PPG sensor 456 may be slightly embedded inside of the gasket 452 and disposed to illuminate light into, for example, supraorbital artery region 402 (shown in FIG. 13). The piezoelectric sensors 458 and 460 may be disposed on top of the gasket 452 and positioned to contact, for example, the first angular artery region 404, the second angular artery region 406, a temporal artery region 407, or combination thereof. The sensors 458, 460 are shown as square piezoelectric sensors, but other shapes may be used (e.g., circular shapes, oval shapes, trapezoidal shapes, multiangular shapes, or combination thereof). It is to be understood that the sensors 456, 458, and/or 460 may be placed at any location on the gasket 452, and that one, two, three, four, five, or more sensors may be used. Further, the sensors may include any sensor type previously described with respect to sensors 32 and/or 64.

Figure 15:
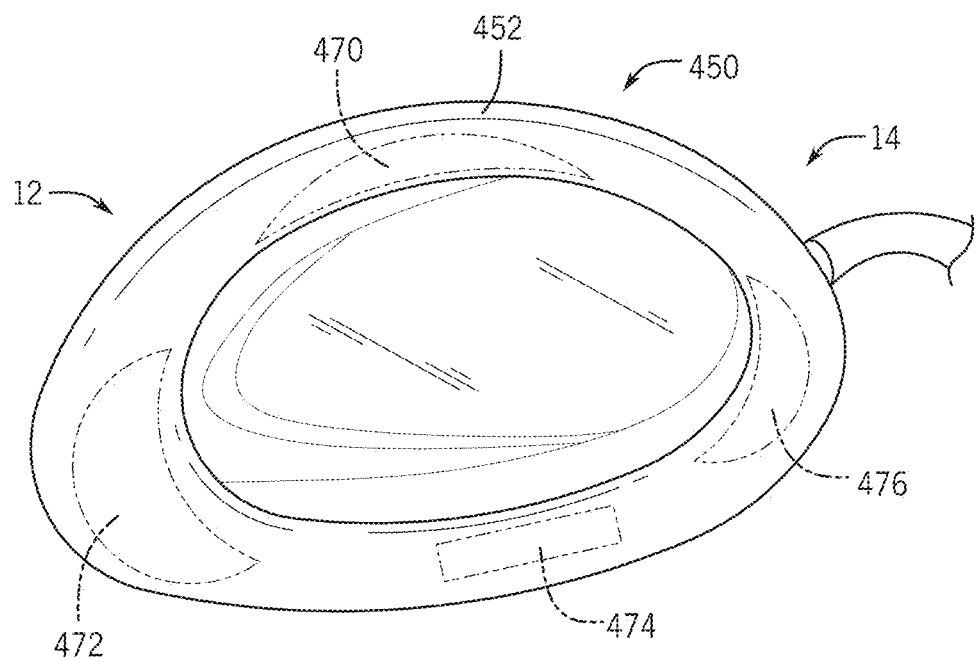
FIG. 15 is a rear perspective view of another embodiment of the MIDS of FIG. 1 when provided in a swim goggles form factor.

FIG. 15 is a rear perspective view of another embodiment of the MIDS 12 when provided in a swim goggles 14 form factor. In the depicted embodiment, four piezoelectric sensors 470, 472, 474, and 476 are shown. The piezoelectric sensors 470, 472, 474, and 476 are disposed to cover a wider area of the gasket 452 when compared to FIG. 14. The piezoelectric sensors 470, 472, and 476 are also shown as being multi-angled sensors covering more surface area when compared to the piezoelectric sensors 458, 460 of FIG. 14. During operations, the piezoelectric sensors 470, 472, 474, and 476 may each provide a signal correlative with cardiac rhythm or heart rate. The signals from the piezoelectric sensors 470, 472, 474, and 476 may then be processed by the processor(s) 50 and converted into measurements such as heart rate.

Figure 16:
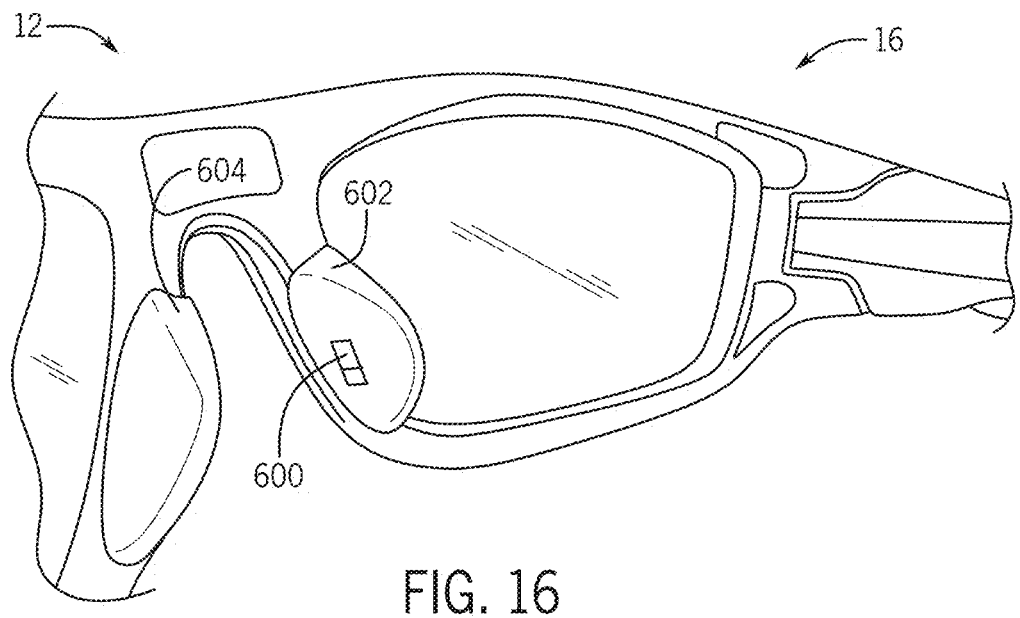
FIG. 16 is a rear perspective view of an embodiment of the MIDS of FIG. 1 when provided in a sunglass or eyeglass form factor.

FIG. 16 is a rear perspective view of an embodiment of the MIDS 12 when provided in a sunglass 16 form factor. In the depicted embodiment, one PPG sensor 600 is shown disposed on a nose bridge pad 602 of the sunglass 16. A second nose bridge pad 604 is also shown. In some embodiments, a second sensor (e.g., PPG or piezoelectric sensor) may be disposed on the second nose bridge pad 604. The PPG sensor 600 may illuminate a nose bridge region and used as described above to derive a variety of measurements, including heart rate, cardiac cycle stages (e.g., 1 Isovolumic relaxation, 2a Inflow: (Ventricular filling), 2b Inflow: (Ventricular filling with Atrial systole), 3 Isovolumic contraction, 4 Ejection: Ventricular ejection), respiration (e.g., due to variance in the intrapleural pressure), fluid volumes and so on. In addition to or alternative to the PPG sensor 600, a piezoelectric sensor may be used, as shown in FIG. 17.

Figure 17:
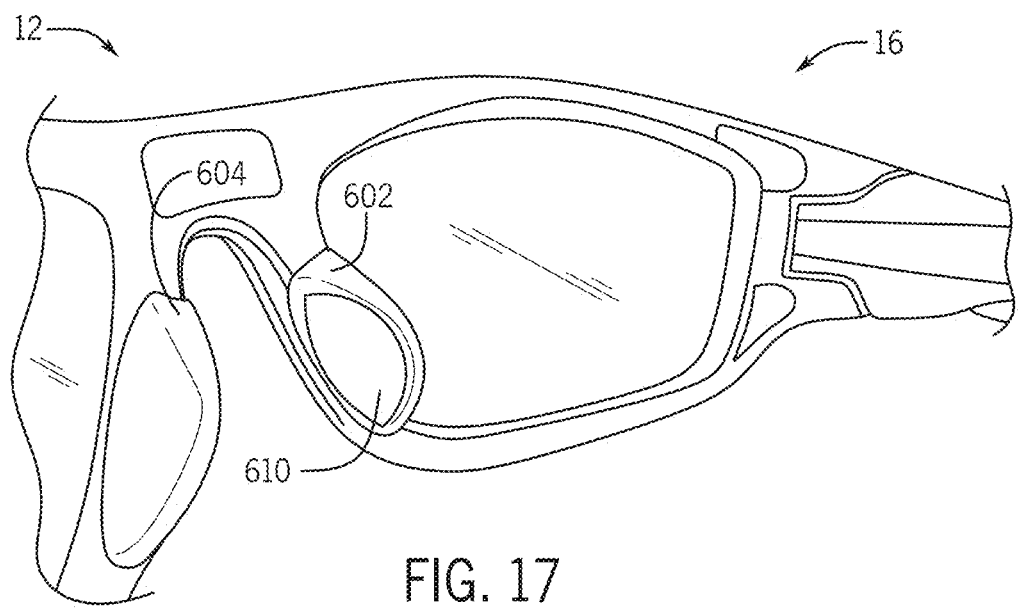
FIG. 17 is a rear perspective view of another embodiment of the MIDS of FIG. 1 when provided in a sunglass or eyeglass form factor.

FIG. 17 is a rear perspective view of another embodiment of the MIDS 12 when provided in a sunglass 16 form factor. In the depicted embodiment, one piezoelectric sensor 610 is shown disposed on the nose bridge pad 602 of the sunglass 16. The second nose bridge pad 604 is also shown. In some embodiments, a second sensor (e.g., PPG or piezoelectric sensor) may be disposed on the second nose bridge pad 604. The PPG sensor 610 may use the piezoelectric effect to detect cardiac rhythms in the nose area, and then derive various measurements as previously described.

Figure 18:
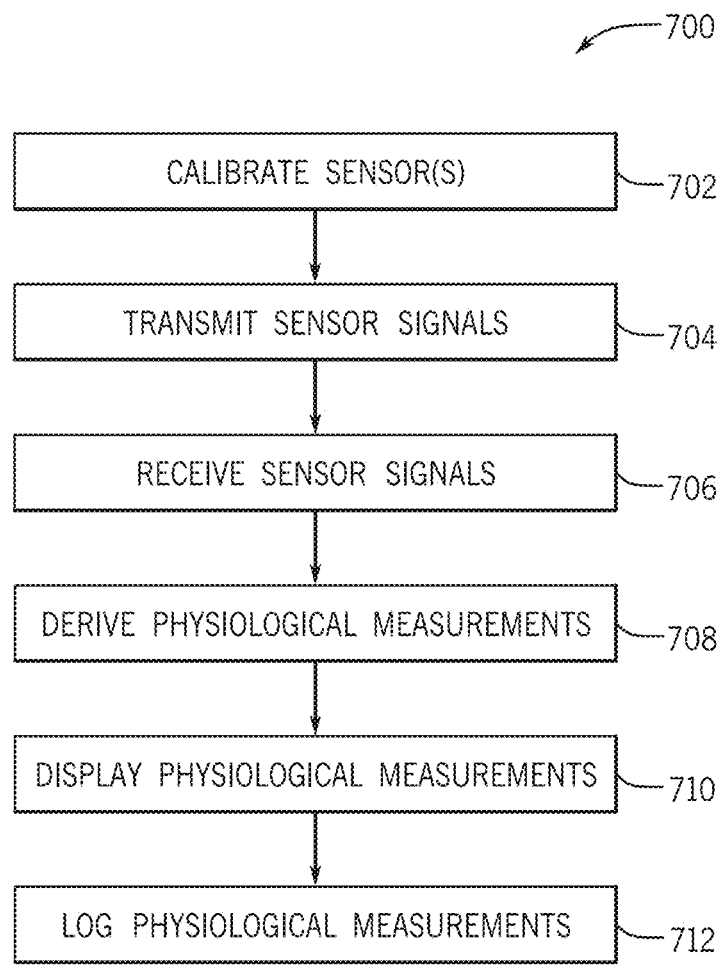
FIG. 18 is a flowchart of an embodiment of a process suitable for deriving one or more physiological measurements.

FIG. 18 is a flowchart of an embodiment of a process 700 suitable for deriving one or more biological measurement for the user of the MIDS 12. The process 700 may be implemented as computer code or instructions executable by the processor(s) 50 and stored in the memory 52. It is to be understood that not all of the blocks shown may be performed by the process 700 and some of the blocks may be performed in other orders instead of the one shown. In the depicted embodiment, the process 700 may calibrate (block 702) certain sensors, such as the sensors 32 and/or 64. For example, when a swimmer dons the MIDS 12 (e.g., goggles 14), the swimmer may adjust the MIDS 12 to provide a watertight fit. When placed on the user and/or when requested by the user, the MIDS 12 may calibrate (block 702) the sensors 32 and/or 64 to account for environmental conditions, for example.

The process 700 may then transmit (block 704) sensor 32 and/or 64 sensor signals. That is, during operations, the sensors 32 and/or 64 may transmit signals correlative of certain physiological measurements, such as but not limited to heart rate, cardiac rhythm, cardiac cycle stages (e.g., 1 Isovolumic relaxation, 2a Inflow: (Ventricular filling), 2b Inflow: (Ventricular filling with Atrial systole), 3 Isovolumic contraction, 4 Ejection: Ventricular ejection), respiration (e.g., due to variance in the intrapleural pressure), fluid volumes and so on. The transmitted signals may be received (block 706) by the processor(s) 50, by signal processors (e.g., digital signal processors [DSPs]), by external systems (e.g., mobile devices 34, cloud-based system 36, external computing systems 37), and the like.

The process 700 may then derive (block 708) one or more physiological measurements, for example, during activities involving the MIDS 12. As mentioned earlier, heart rate, cardiac cycle, respiration, hypovolemia, hypervolemia, calories burned, heart rate, cardiac heart rest recovery time, health recovery time, heart variability, and so on. The derived measurements may then be displayed (block 710), for example, via the display 58 and/or displays included in external systems (e.g., mobile devices 34, cloud-based system 36, external computing systems 37). When displayed by the display 58, a user, such as a swimmer, may easily visualize current heart rate, respiration, calories, burned, and so on, without having to add extra equipment (e.g., chest sensors, limb sensors). The process 700 may additionally log (block 712) the physiological measurements, for example to then provide a historical view of a training sessions, user progress, changes in technique and consequent impact to physiological measurements (e.g., changes in heart rate after changing swim stroke patterns), and so on.

Figure 19:
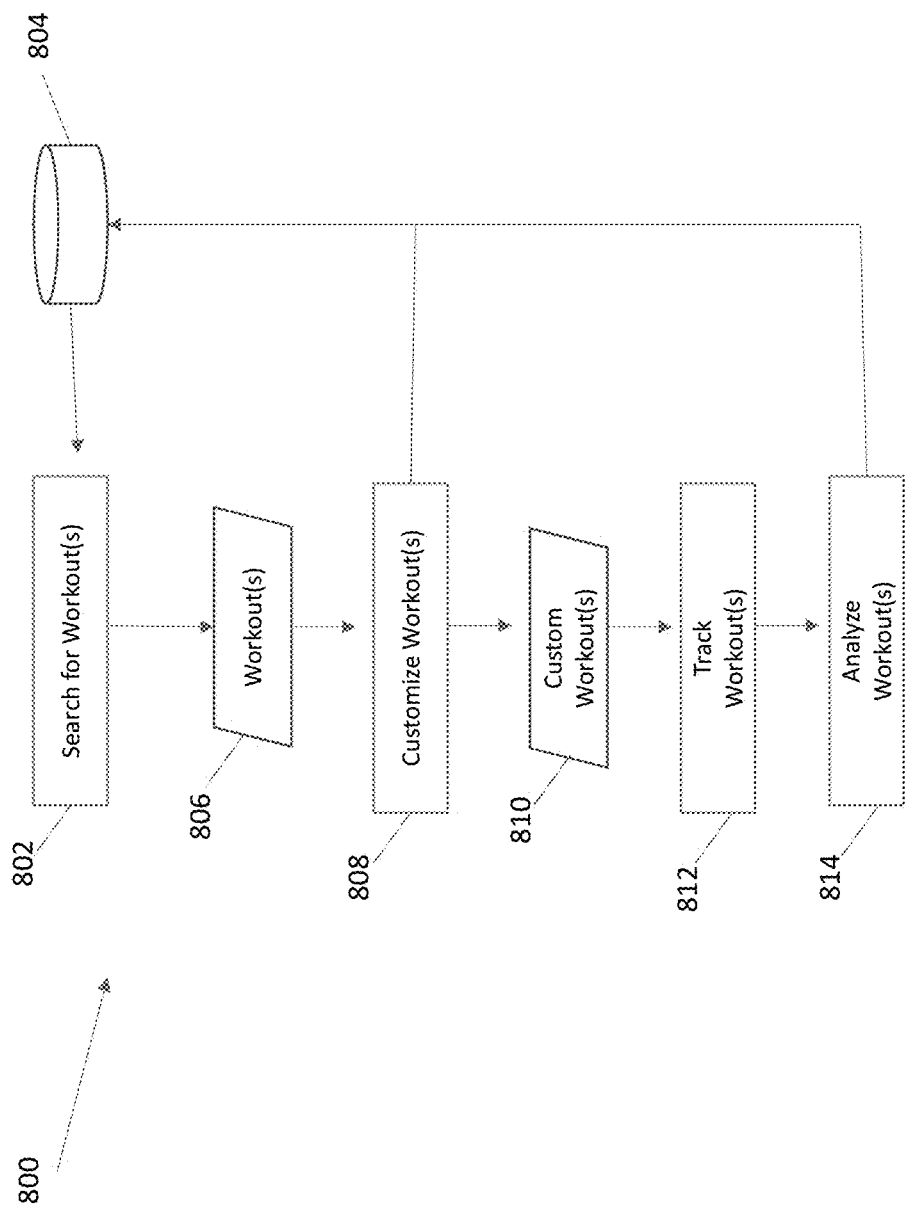
FIG. 19 is a flowchart of an embodiment of a process suitable for applying workout techniques via the MIDS of FIG. 1.

FIG. 19 is a flowchart of an embodiment of a process 800 suitable for applying workout techniques via the MIDS 12. The process 800 may be implemented as computer code or instructions executable by the processor(s) 50 and stored in the memory 52. It is to be understood that not all of the blocks or steps shown may be performed by the process 800 and some of the blocks or steps may be performed in other orders instead of the one shown. In the depicted embodiment, a user may search (block 802) for one or more existing workouts. For example, the user may search for workouts that have been stored in a data repository 804. The data repository 804 may be included in the cloud-based system 36, as part of storage (e.g., memory 52) of the MIDS, as part of storage of the mobile device 34, as part of storage of external computing systems 37, or a combination thereof.

Searching for workouts (block 802) may include searching for workout phases and/or attributes stored in each workout. The workout phases and/or attributes may define a workout, and may include workout duration, workout distance, effort to be expended, and so on. Each phase and/or attribute may include a metric based on a particular sport or sports. For example, for swimming, distance may include total distance in pool laps, in yards, in miles, and so on, which may be based on indoor (e.g., pool swim) environments and/or outdoor swim environments. Likewise, a cycling and/or running distance may include number of miles or kilometers, number of laps in a track (or other circuit), or a combination thereof. Workout duration metrics may include time metrics in seconds, hours, minutes, days, or combination thereof, rest intervals (e.g., time to rest between a second activity or set), and so on. Effort to be expended attributes may include textual descriptions ("easy", "medium", "hard", "strong", "very strong", "progress effort"), as well as metrics such as heart rate (e.g., beats per minute), pulse oximeter metrics (e.g., SpO2), calories, and the like.

As mentioned earlier, phases and/or attributes for a workout may vary based on sport. For example, in swimming, phases and/or attributes may include a swim style (e.g., freestyle, butterfly, backstroke, breaststroke, sidestroke, elementary backstroke, combat sidestroke, trudgen), a send off time (e.g., time to complete a swim, rest, and then begin another swim), a rest (time to rest), bilateral breathing (e.g., breathing on alternate sides, such as every third or fifth stroke), a build-up swim (e.g., specific distance over which speed is increased gradually), a drill (e.g., focusing on a component or components of a swim, such as hand entry into water, head positioning, and so on), a cool down (e.g., easy to moderate swimming for example, following a more intensive swim), an ascending interval (e.g., a set or workout in which the interval [swim time plus rest] increases with each repeat), a decreasing interval (e.g., a set or workout in which the interval decreases with each repeat), an ascending set (e.g., a series of swims of the same distance in which swim time increases with each repeat), a descending set (e.g., a series of swims of the same distance in which swim time decreases with each repeat), a distance per stroke (e.g., distance covered per stroke), a negative split (e.g., swim during which the second half is completed faster than the first half), a pace (e.g., average time for a specific distance within a specific swim style such as freestyle), pulling (e.g., swimming using upper body only), a set (e.g., a number of repetitive swims (repeats) at specific distances that typically involve an interval or a specific amount of rest, an example of a basic set is 10×100s@1:30 which could be interpreted to mean swimming 100 yards or other distance metric and resting after the swim, where the total swim and rest time does not exceed one minute 30 seconds, and doing 10 of the swim/rest combinations), sprint (e.g., swimming at top speed in any given stroke), a warmup (e.g., a period of swim time to acclimate muscles usually to then follow up with faster swimming). Similar phases and/or attributes may be provided for other sports, such as cycling, running, triathlon, snowboarding, skating, motor sports, and so on.

Searches may also be performed based on sport ability, such as beginner, intermediate, advanced. Additionally or alternatively, searches may be performed by coach's name, athlete name, social media group or individual, club name, organization name, and so on. In some embodiments, analysis or previous workouts and progress made may be used so that the workouts are suggested. For example, based on meeting certain goals (e.g., meeting workout duration, distance, and/or effort expended goals), a new workout or workouts may then be suggested. Workouts may be linked to each other. That is a first workout may include a link to a second workout, and/or vice versa. Accordingly, a chain of workouts may be provided. The chain may begin at a workout having a lesser workout duration, distance, and/or less effort expended, and move up the chain to workouts with longer workout duration, distance, and/or more effort expended.

Selected workouts 806 may then be downloaded (or filtered) to be viewed and monitored by the MIDS 12. In some embodiments, the workouts may be customized (block 808). For example, the user may use the MIDS 12 (or other device such as mobile device 34, external systems 37) to change one or more of the workout duration, distance, and/or more effort expended. Indeed, any workout attribute may be customized. Customization (block 808) may be done via the MIDS 12, for example through input buttons provided, or by interfacing the MIDS 12 to the mobile device 34, cloud 36, and/or external systems 37.

For example, for a workout that is in a 25 yard pool, a workout having a phase "10×100@1:20" would be interpreted as swimming 4 laps of the pool or 100 total yards in 1 minute 20 seconds or less. If the user swims the 100 yards in 1 minute 10 seconds, then 10 seconds are used for rest. The user repeats the swim/rest 9 more times. If the user can only swim a 100 on a time of 1 minute 50 seconds, the workout may be adjusted (e.g., automatically adjusted by the MIDS 12) to become 10×100@1:50 instead. If the user is in a different length pool the workout may also be adjusted (e.g., automatically adjusted by the MIDS 12), for example, by changing the time to account for the user's ability in a given pool length.

The table below shows an example workout matrix of phases and attributes,

TABLE 1

Workout Phase/Attribute Examples

Guided Workout
    1..N Workout
    Section or
    Phase (sets)
        1..N Workout Item
            Repeat Count value
            Distance value
            Swim Style
            Rest value
            Pace value
            Stroke Rate value
            Modifier In Table 1, a first column shows that the workout is a guided workout. That is, the workout may be guided through the MIDS 12. The guided workout may then include one or more workout phases or sections in column 2. Each of the workout phases or sections (e.g., sets) may then include 1 or more workout items or attributes in column 3, and the values for each attribute may be stored, for example, in column 4. In one embodiment, a graphical user interface (GUI) may present a table similar to Table 1 for customization. The user may scroll through the workouts 806 in the table and then customize (block 808), for example, values in column 4 to then save the changes as customized workouts 810. Other customization may include deleting a row (e.g., thus removing a workout phase or attribute), adding a row (e.g., adding a new phase or attribute), and so on. The customized workouts 810 may then be saved to the repository 804.

The workouts 806 and/or customized workouts 810 may then be tracked (block 812). For example, the user may don the MIDS 12 and then proceed to use the MIDS 12 to perform the workout. As the user performs the workout (e.g., swims, runs, cycles, skis, and so on), the MIDS 12 may then track the phases and/or attributes for the workout, such as distance, duration, effort expended, and the like.

The MIDS 12 may also provide support for the workout, such as guiding the user through the workout by displaying certain information textually, graphically (e.g., via images/video), via LEDs, or a combination thereof. In certain embodiments, certain metrics such as stroke rate is monitored, and the MIDS 12 may then emit an LED pulse at that rate allowing for a visual queue for the user to take a stroke. Further, the MIDS 12 may fine tune this rate to the person's abilities. By measuring the user's current stroke rate the MIDS 12 may increase it by an amount (e.g., 1-15%) such that it is attainable for the person. Consequently, the MIDS 12 may adjust the rate if the person can't keep up or if the rate is too easy. Indeed, automated coaching may be provided by adjusting workouts 806 and/or 810 based on abilities. For example, if workout called for 10×100@1:20 and the user can barely make that time, then the MIDS 12 will adjust the workout to a better interval, mix in recovery sets like a 50 (e.g., 50 meters instead of 100 meters using the same stroke and time), rest intervals, etc., automatically during the workout.

The MIDS 12 may also incentivize the user during the workout, for example, if the user is within a personal best, the MIDS 12 may display a message such as "5 secs from personal best" and/or change stroke rate (e.g., via LED) to push you to improve on the personal best. Indeed, leaderboard/goal based inspiration and feedback may be provided. For example, the MIDS 12 may communicate with and/or use data from various social media/external systems such as Strava, MySwimPro, Swim.com app, Swim IO, Swim4Gold, and so on, and retrieve king/queen of the mountain (KOM/QOM) goals, trophies, medals, laurels, personal bests, personal bests of social media users, of clubs, of friends, of other entities, and dynamically display them as the user performs the workout.

The MIDS 12 may also provide real-time awareness of friends, social media contacts, professional athletes, and so on, both real and virtual. For example: if the user is riding a certain hill and the user is trying to beat you're a certain person's time, the MIDS 12 may show your time versus the other person's in real time as you are making the effort (e.g., virtual racing). Likewise, you both persons may be riding that hill at the same time and the MIDS 12 may then you the time delta between the two of you (e.g., real time racing). Same functionality is provided for other sports, such as swimming, running, skiing, motor sports, walking, and so on.

Example information displays are shown with respect to FIG. 21 below. It is to be noted that "linked" workouts may be provided, for example, for multi-sport activities. For example, for triathlon activities, the user may link swim workouts to be followed by cycling workouts to be followed by running workouts. Several MIDS 12 may be used during this linked workouts. For example, a first MIDS 12 may be disposed in swim goggles and as the user transitions to a second MIDS 12 disposed in sunglasses the two MIDS 12 may handshake (e.g., communicate via Bluetooth, WiFi, near field communications, and so on) so that the first MIDS 12 transfers data to the second MIDS 12, including all data sensed during the swim portion of the workout. Accordingly, some metrics like total calories expended during the swim, bike, and/or run, average heart rate, and the like, may be visualized via the second MIDS 12 that account for all multi-sport activities captured via the first MIDS 12.

The process 800 may then save data gathered during the workout, including duration, length, effort expended, and/or other workout phase/workout attributes, as well as date, time, location (e.g., GPS location(s) of user during workout). The data may then be analyzed (block 814). For example, physiological metrics such as heart beat, SpO2, breathing rate, breathing type (e.g., times and/or GPS location side breathing and/or bilateral breathing was used), calories burned, and so on, may be used, as well as the workout phase/attributes (e.g., duration, length, effort expended), during the workout analysis (block 814). The analysis may be sport specific and thus include derived metrics for a specific sport. In swimming, some examples include time spent at a given swim stroke, swim stroke analysis (e.g., via the sensors 64, GPS 66, IMU 68), pace, stroke rate, stroke distance, body drag profile, amount of propulsive force applied, duration of propulsive force, turn efficiency, kick cadence, distance per kick, and so on. For cycling some example include power output at the crank, revolutions per minute (RPM), cadence, pedal speed, pedal force, body positioning, etc. For running some examples include, running cadence, body positioning (e.g., head position, back angle, knee height), kick distance, foot pronation, breathing rate, and so on. The analysis may provide reports on progress, identification of plateauing, identification on areas for improvement, and the like. The analysis may be stored in the data repository 804, for example, for collaborative coaching, sharing of workout results in social media, attending virtual competitions, and so on. Indeed, the coaching/training system 150, the gaming system 152, the in-competition system 154, and/or the social networking system 156 may be operatively coupled to the data repository 804 to use the data for their respective users.

Figure 20:
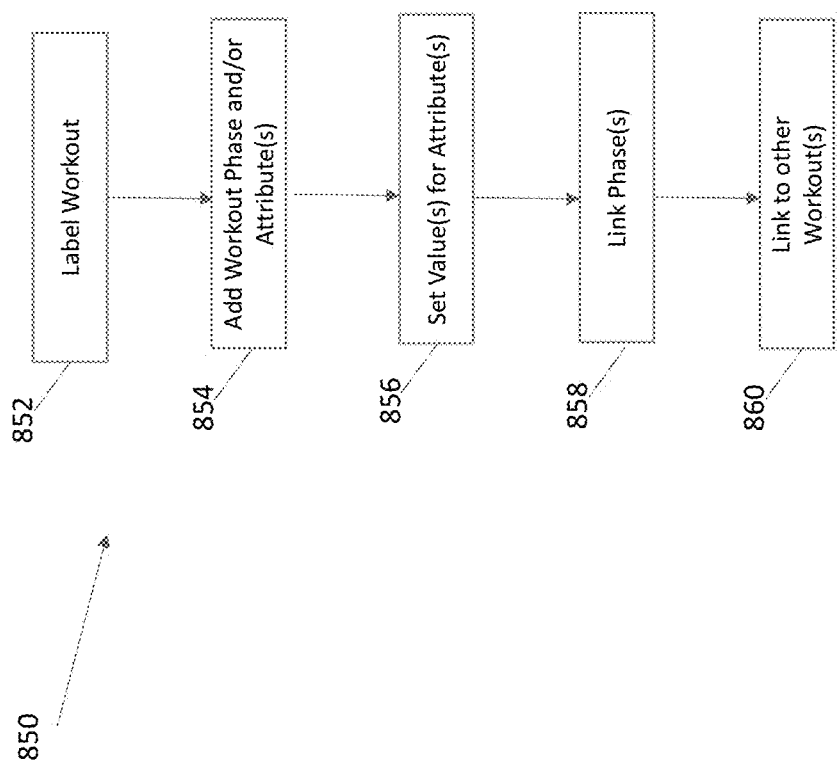
FIG. 20 is a flowchart of an embodiment of a process suitable for creating one or more workouts.

It may be beneficial to show a process for creating a workout in the data repository 804. Turning now to FIG. 20, the figure is a flowchart illustrating an embodiment of a process 850 suitable for creating one or more of the workouts 806. The process 850 may be implemented as computer code or instructions executable by the processor(s) 50 and stored in the memory 52. It is to be understood that not all of the blocks or steps shown may be performed by the process 850 and some of the blocks or steps may be performed in other orders instead of the one shown. In the depicted embodiment, the user may create a workout via the MIDS 12, mobile device 34, cloud system 36, and/or external systems 37. A GUI may be provided, such as a table-based GUI, where the user may first label (block 852) a workout to give it a name, such as "sprint workout."

The user may then add (block 854) one or more workout phases/attributes or other items, for example, by adding rows to the table. More specifically, a new workout may be created via Table-style input, including adding one or more phases and/or attributes for the workout. Other GUIs entry styles may be used to create a workout, such as wizard dialog boxes leading a user through questions, web-based interfaces, and so on. It is to be noted that the phases and/or attributes may be linked (block 858), for example, in sequential order. For example, a first phase and/or attribute such as "send-off time" to 10×100@1:20 may then be linked to a second phase and/or attribute such as "rest" 5 minutes which may then be linked to a third phase and/or attribute such as "send-off time" to 10×100@1:50. Likewise, workouts may also be linked (lock 860). For example, a first swim workout may be linked to a second cycling workout, which may then be linked to third running workout. It is to be noted that the workouts may be linked regardless of sport and/or within the same sport. Accordingly, a flexible workout system may be provided.

Figure 21:
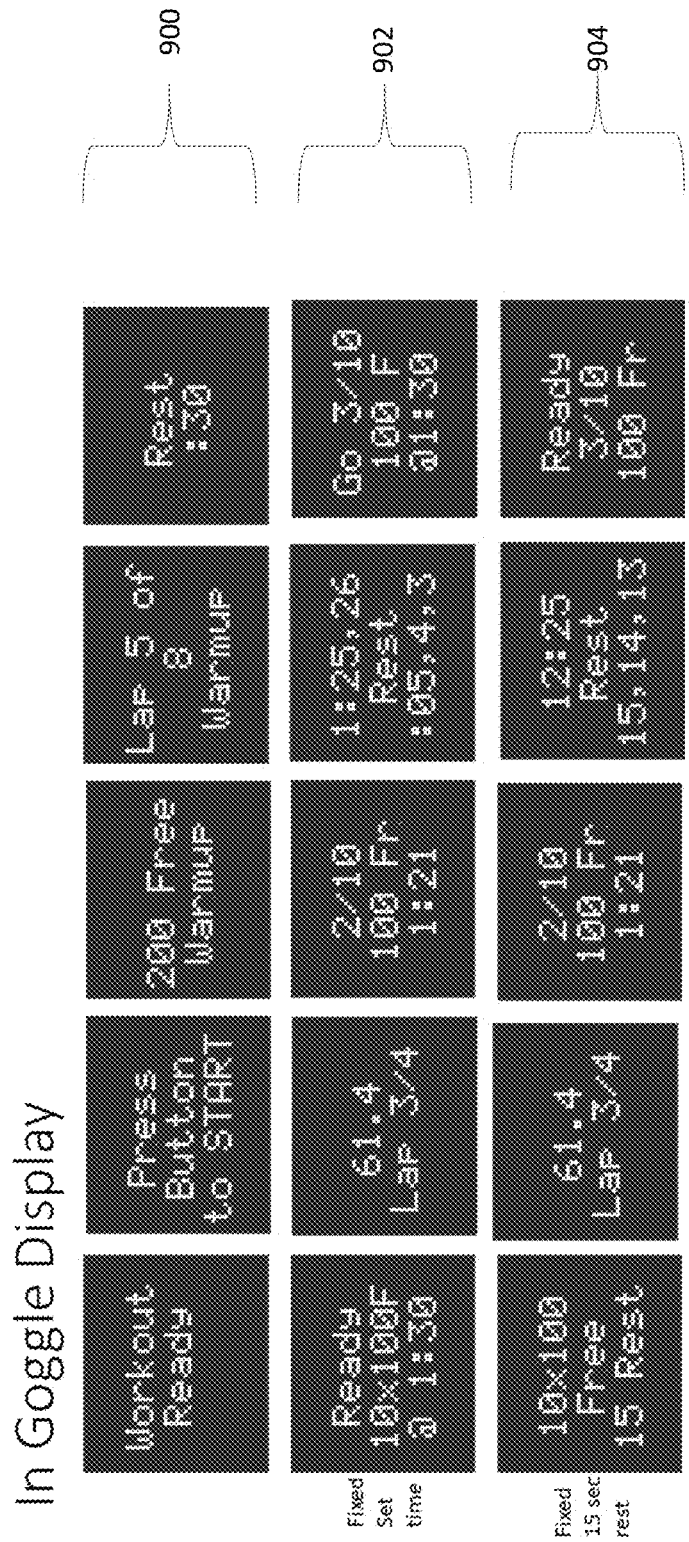
FIG. 21 illustrates a matrix of screenshot embodiments showing workout data.

FIG. 21 is a matrix showing example screenshots for various workout-related screen tiles that may be displayed via the display 58. In the depicted embodiment, the screen tiles are arranged in rows 900, 902, and 904. The display 58 may display each screen tile individually. That is, each screen tile may completely cover the display 58 in certain embodiments. In certain embodiments, For example, for row 900, the user may first download and/or customize a workout into the MIDS and then see a "Workout Ready" screen tile, followed by a "Press Button to START" screen tile. The workout may then being with a warmup, so a "200 Free Warmup" screen tile may be displayed, denoting a 200 yard freestyle warmup swim. As the user swims the warmup, laps may be automatically counted and displayed. For example, the figure shows a "Lap 5 of 8 Warmup" screen tile during the fifth lap of the warmup swim. At the end of the warmup, a "Rest 30" screen tile may be shown, instructing the user to rest for 30 seconds.

The workout may include fixed set times and/or fixed rest times. For fixed set times, row 902 shows that after the warmup, the display 58 may show a "Ready 10×100F@1:30" screen tile representative of swimming 100 yards freestyle at 1 minute 30 seconds with rest included, and doing so 10 times. As the user swims, the MIDS 12 has been appraised of certain information such as pool length, and thus can derive how much distance has been covered, showing a "61.4 Lap 3/4" screen tile denoting that the user is in a third lap of a 4 laps (e.g., in a 25 yard pool), and has swam 61.4 yards. As the user finishes the first of 10 sets and stops, the MIDS 12 detects the swim pause and the end of the first 100 yards. Accordingly, the display 58 then reads "2/10 100 Fr 1:21" denoting that the user has swam freestyle the second of the 10 sets in one minute 21 seconds. The user may now rest for 9 seconds (e.g., 1:30-1:21). As the user rests, the display 58 may count down, for example, with a screen tile showing "1:25, 26 Rest :05, 4, 3" until the countdown reaches zero and the user then begins the third of 10 sets.

As shown, row 904 is displaying the use of fixed rest times. For example, a "10×100 Free 15 Rest" screen tile may first be displayed. The user may thus swim 100 yards, rest for 15 seconds regardless of the time spent swimming, and swim another 9 sets always resting 15 seconds between sets. In the depicted embodiment, a "61.4 Lap 3/4" screen tile is also shown, denoting that the user is in a third lap of a 4 laps (e.g., in a 25 yard pool), and has swam 61.4 yards. A "2/10 100 Fr 1:21" screen tile is then shown, denoting that the user has swam freestyle the second of the 10 sets in one minute 21 seconds. However, because this workout is a fixed rest time, a screen tile displays "12:25 Rest 15, 14, 13" to denote that 12 minutes 25 seconds have elapsed and that the user is now resting for 15 seconds (e.g., via a countdown that will count from 15 seconds down to zero). When the countdown is over, a screen tile "Ready 3/10 100 Fr" is then shown, letting the user know that the user may now proceed with the third set of 10 swims. It is to be noted that the MIDS 12 may detect the user stopping by using sensors 64, GPS 66, and/or IMU 68, for example, and then provide a suitable display, such as a rest countdown, to move to the next sequence in the workout, and so on. Buttons 56 and/or head movements (e.g., head shake gestures) may also be used to pause a workout, and/or to move the workout to the next sequence. In some embodiments, each screen tile is representative of a workout phase, which may include one or more attributes. By guiding a user sequentially through one or more screen tiles, the techniques described herein may guide a user through a more efficiently monitored workout.

Figure 22:
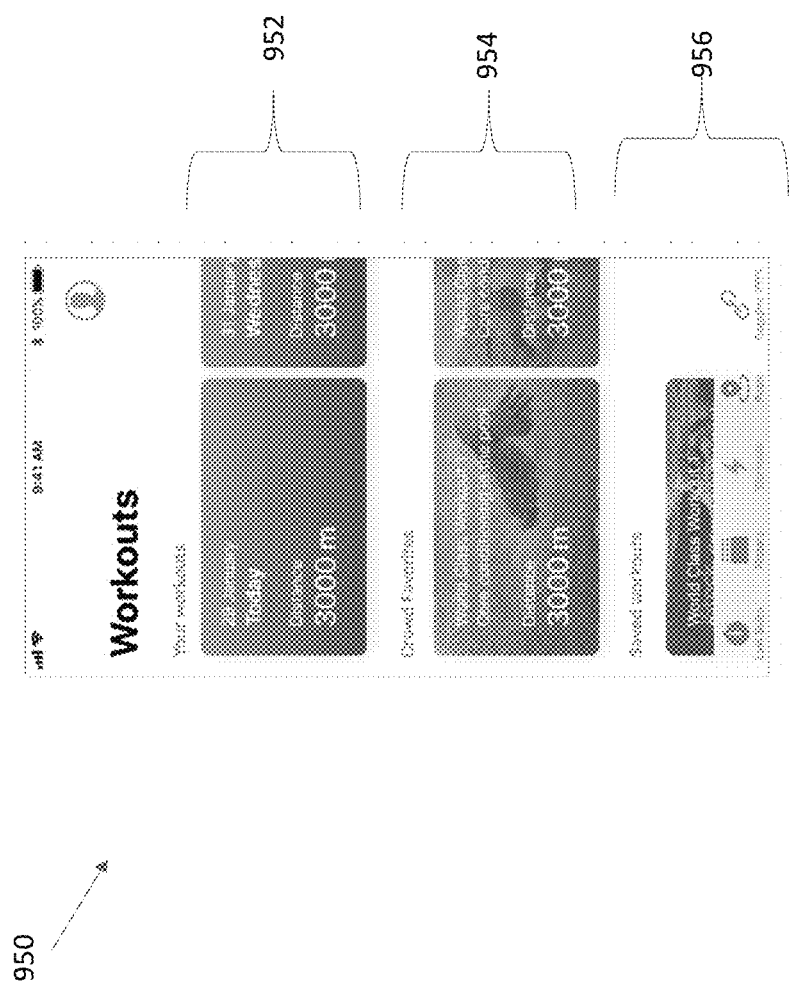
FIG. 22 is a screenshot of an embodiment of a software application for displaying certain workout data.

Turning now to FIG. 22, the figure is a screenshot of an embodiment of a software application 950 (e.g., app 164) that may be executed and/or displayed in a mobile device 34, inside a web browser, on computer, in a smart watch, and so on. In the depicted embodiment, the application 950 may be divided into various workout sections 952, 954, 956. Section 952 may be used as "Your workouts" to display a list of the workouts 806 and/or 808 that the user has access to, for example, via the data repository 804. Section 954 may be used for "Crowd Favorites" to display, for example, workouts 806 and/or 808 that the user's friends, club, organization, social media followers/following, and so on, have selected as favorites. Section 956 may be used to list workouts 806 and/or 808 that have been performed, for example, for later review and/or analysis.

Figure 23:
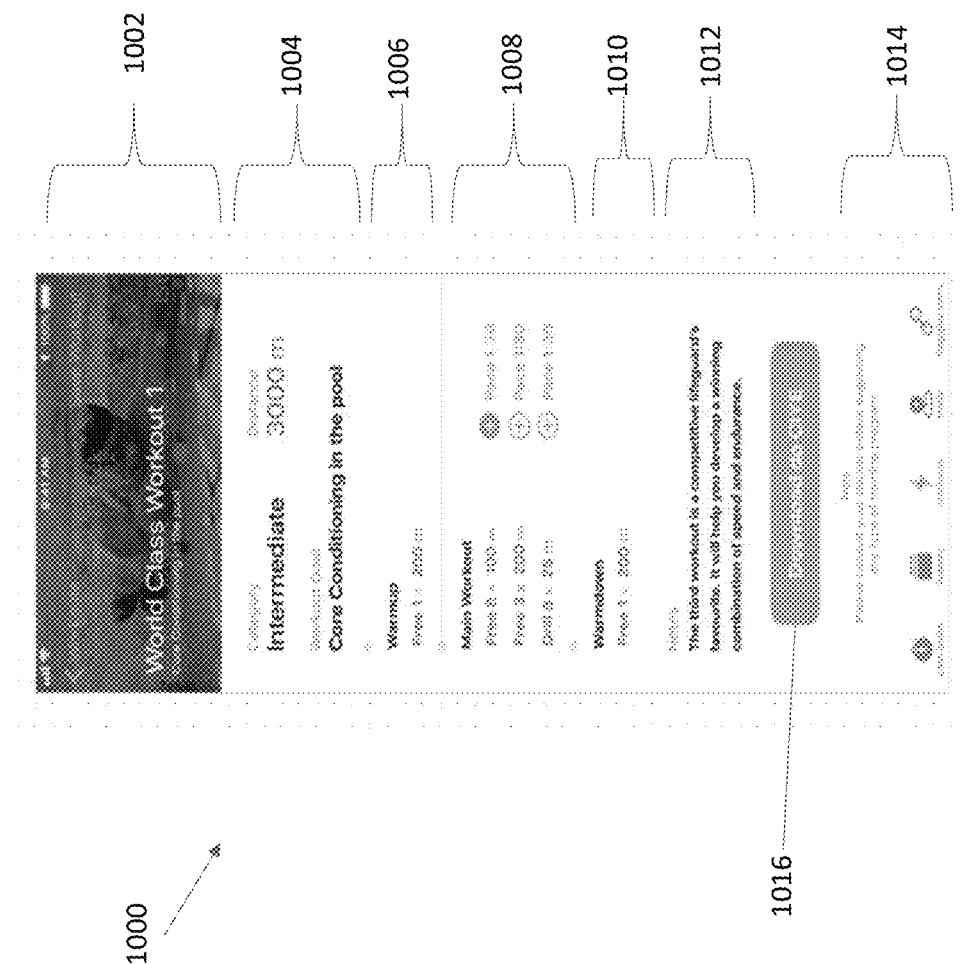
FIG. 23 is a screenshot of an embodiment of a software application for displaying and customizing certain workout data.

FIG. 23 is a screenshot of an embodiment of a software application 100 (e.g., app 164) that may be executed and/or displayed in a mobile device 34, inside a web browser, on computer, in a smart watch, and so on. In the depicted embodiment, the application 1000 may include a section 1002 to be used, for example, in displaying the name of the workout 806 and/or 808, a short workout description, and may additionally include GUI controls for saving changes to the displayed workout 806 and/or 808 as well as to navigate to other applications or application screens.

The application may further include a section 1004 that may display a workout category (e.g., beginner, intermediate, advanced), as well as a workout total distance and a workout goal. Several sections may then be provided to list and/or customize the workout. For example, the illustrated embodiment shows sections 1006, 1008, 1010, and 1012. The user, for example, may type or otherwise enter values for certain workout attributes. In the depicted embodiment, GUI controls (e.g., + sign, − sign, arrows, textboxes, and so on) may be used to adjust certain of the attributes. For example, swim pace is shown as being adjustable via + controls. Likewise, section 1010 may include further workout attributes (e.g., warmdown distances and/or time) that may be user adjustable.

Section 104 may include other controls, such as controls to visualize the last swim, controls to see a history of swims, controls to find pools in a map, controls to search workouts, and/or controls to link with the MIDS 12, for example, to download workouts into the MIDS 12. In the depicted embodiment, once the workout is customized, the user may then press a download button 1016 to send the workout to the MIDS 12.

Figure 24:
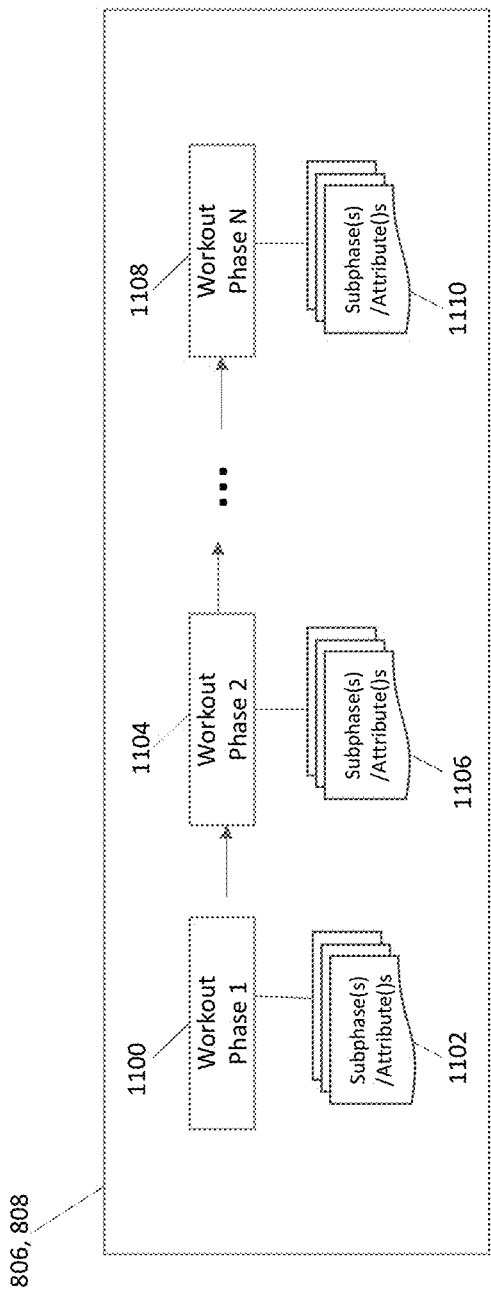
FIG. 24 is a block diagram an embodiment of a workout that may have one or more workout phases and attributes.

FIG. 24 is a block diagram of an embodiment of a workout 806 and/or 808 that may have one or more workout phases and attributes. In the depicted embodiment, a workout phase 1102 is shown as having attributes 1102. For example, the workout phase may be a warmup, and the attribute(s) may include a length and/or time to perform the warmup. The workout phase 1102 may then be linked (e.g., sequentially linked to a workout phase 1104, such as a main workout phase. The main workout phase 1104 may have several subphases and/or attributes 1106, such as a first subphase "8×100 m Free@1:30", followed by a second subphase "3×200 m Free@2:30", followed by a third subphase "Drill 8×25 m@1:00". The workout phase 1104 may then be linked to other workout phases, until a final workout phase 1108 may be reached. The final workout phase 1108 in the depicted embodiment, may include a warmdown phase having subphases and/or attributes 1110 such as a "1×200 m." As mentioned earlier, each workout phase 1100, 1104, 1108 may one or more screen tiles, such as the tiles in rows 900, 902, 904, that may display information to the user when the user is performing the workout phase.

Technical effects of the invention include providing for a minimally intrusive display system that may be disposed in a variety of eyewear to provide for feedback during certain activities, including sports activities. The minimally intrusive display system may derive certain metrics and performance measures during performance on an activity, and then display the metrics and performance measures to a wearer of the eyewear. Haptic and audio feedback may also via provided via the minimally intrusive display system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a minimally intrusive display system (MIDS) configured to be disposed on an eyewear, the MIDS comprising:
  a waterproof container configured to be disposed between a lens of the eyewear and an eye of a user of the eyewear;
  a battery system configured to provide power for the MIDS, wherein the battery system is disposed within the waterproof container;
  a display system disposed within the waterproof container and configured to be disposed between the lens of the eyewear and the eye of the user of the eyewear;
  a sensor system included in the eyewear configured to provide sensor data; and
  a processor configured to:
    download a workout;
    adjust the workout to provide a customized workout;
    process the sensor data to monitor the user wearing the MIDS during the customized workout; and
    display, via the display system, a workout progress based on the monitoring, wherein the workout progress comprises text associated with the customized workout.

2. The system of claim 1, wherein the workout progress comprises a workout duration, a workout distance, a workout effort, or a combination thereof, for swimming, bicycling, running, skiing, walking, motorsporting, or a combination thereof.

3. The system of claim 1, wherein the eyewear comprises swim goggles, and wherein the workout comprises a swimming workout having workout phases and/or workout attributes comprising a swim style, a send off time, a bilateral breathing, a build-up swim, a warmup, a cool down, an ascending interval, a decreasing interval, an ascending set, a descending set, a distance per stroke, a negative split, a pace, a pulling, a set, a drill, a sprint, or a combination thereof.

4. The system of claim 1, wherein the workout is configured to be stored in a data repository to be searched via a workout phase, a workout attribute, a social network, a club, a coach, an entity, a workout facility, a second user, or a combination thereof.

5. The system of claim 1, wherein processor is configured to save the customized workout in an external data repository.

6. The system of claim 1, wherein the workout comprises one or more workout phases linked sequentially.

7. The system of claim 1, wherein the processor is configured to display, via the display system, a workout phase of the customized workout representative of the user performing the workout phase.

8. The system of claim 1, wherein the customized workout comprises one or more workout phases linked sequentially.

9. The system of claim 1, comprising a second workout linked to the customized workout, wherein the processor is configured to process the sensor data to monitor the user wearing the MIDS during the second workout; and display, via the display system, a second workout progress based on the monitoring of the user during the second workout.

10. A non-transitory computer readable medium comprising executable instructions which, when executed by a processor, cause the processor to:
   download a workout from a data repository, wherein the workout is downloaded based on user selection of the workout from the data repository;
   receive sensor data from a sensor system disposed in a minimally intrusive display system (MIDS) configured to be disposed on an eyewear, the MIDS comprising a waterproof container, a battery system disposed within the waterproof container and configured to provide power for the MIDS, a display system disposed within the waterproof container, and the processor, wherein the waterproof container is configured to be disposed between a lens of the eyewear and an eve of a user of the eyewear;
   process the sensor data to monitor the user wearing the MIDS during the workout;
   display, via the display system, a workout progress based on the monitoring; and
   display, via the display system, textual information associated with the workout.

11. The non-transitory computer readable medium of claim 10, wherein the executable instructions, when executed by the processor, cause the processor to search the data repository before the user selection of the workout to retrieve a list of workouts from the data repository.

12. The non-transitory computer readable medium of claim 11, wherein the executable instructions, when executed by the processor, cause the processor to search the data repository by a workout phase, a workout attribute, a social network, a club, a coach, an entity, a workout facility, a second user, or a combination thereof.

13. The non-transitory computer readable medium of claim 10, wherein the executable instructions, when executed by the processor, cause the processor to customize the workout to produce a customized workout.

14. The non-transitory computer readable medium of claim 10, wherein the executable instructions, when executed by the processor, cause the processor to create a new workout and to store the new workout in the data repository.

15. The non-transitory computer readable medium of claim 10, wherein the executable instructions, when executed by the processor, cause the processor to:
   process the sensor data to monitor the user wearing the MIDS during a second workout; and
   display, via the display system, a second workout progress based on the monitoring of the user during the second workout,
   wherein the second workout is sequentially linked to the workout.

16. The non-transitory computer readable medium of claim 10, wherein the executable instructions, when executed by the processor, cause the processor to automatically adjust the workout during the workout based on the sensor data.

17. A method, comprising:
   searching a data repository for a workout by a workout phase, a workout attribute, or both;
   downloading the workout from the data repository based on a user selection of the workout;
   receiving a sensor data from a sensor system disposed in a minimally intrusive display system (MIDS) configured to be disposed on an eyewear, the MIDS comprising a waterproof container, a battery system disposed within the waterproof container and configured to provide power for the MIDS, a display system disposed within the waterproof container, wherein the waterproof container is configured to be disposed between a lens of the eyewear and an eve of a user of the eyewear, and a processor;
   processing the sensor data to monitor the user wearing the MIDS during the workout; and
   displaying, via the display system, a workout progress based on the monitoring, wherein the workout progress comprises text associated with the workout.

18. The method of claim 17, comprising searching the data repository for the workout by a social network, a club, a coach, an entity, a workout facility, a second user, or a combination thereof.

19. The method of claim 17, comprising customizing the workout to produce a custom workout.

20. The method of claim 17, comprising creating a new workout, processing the sensor data to monitor the user wearing the MIDS during the new workout; and displaying, via the display system, a new workout progress based on the monitoring of the user during the new workout, wherein the new workout progress comprises additional text associated with the new workout.

* * * * *